United States Patent
McJunkin

(10) Patent No.: US 10,449,055 B2
(45) Date of Patent: Oct. 22, 2019

(54) SYSTEMS AND METHODS FOR TREATMENT OF INTERVERTEBRAL DISC DERANGEMENTS

(71) Applicant: Disc Fix, L.L.C., Paradise Valley, AZ (US)

(72) Inventor: Tory L. McJunkin, Paradise Valley, AZ (US)

(73) Assignee: Disc Fix L.L.C., Paradise Valley, AZ (US)

( * ) Notice: Subject to any disclaimer, the term of this patent is extended or adjusted under 35 U.S.C. 154(b) by 0 days.

(21) Appl. No.: 14/694,222

(22) Filed: Apr. 23, 2015

(65) Prior Publication Data

US 2016/0310286 A1 Oct. 27, 2016

(51) Int. Cl.
*A61F 2/44* (2006.01)
*A61F 2/46* (2006.01)
*A61F 2/30* (2006.01)

(52) U.S. Cl.
CPC ............ *A61F 2/441* (2013.01); *A61F 2/4611* (2013.01); *A61F 2002/3008* (2013.01); *A61F 2002/30011* (2013.01); *A61F 2002/30062* (2013.01); *A61F 2002/3068* (2013.01); *A61F 2002/30069* (2013.01); *A61F 2002/30291* (2013.01); *A61F 2002/30581* (2013.01); *A61F 2002/30586* (2013.01); *A61F 2002/30604* (2013.01); *A61F 2002/444* (2013.01); *A61F 2002/4415* (2013.01)

(58) Field of Classification Search
CPC .. A61F 2/44; A61F 2/441; A61F 2/442; A61F 2/4455; A61B 17/8802; A61B 17/8805; A61B 17/8811; A61B 17/8816; A61B 17/8819; A61B 17/885; A61B 17/8852; A61B 17/8855; A61B 17/8858
USPC ............................ 623/17.11–17.16
See application file for complete search history.

(56) References Cited

U.S. PATENT DOCUMENTS

| | | | |
|---|---|---|---|
| 4,772,287 | A | 9/1988 | Ray et al. |
| 4,904,260 | A | 2/1990 | Ray et al. |
| 6,099,514 | A | 8/2000 | Sharkey et al. |
| 6,224,630 | B1 | 5/2001 | Bao et al. |
| 6,240,926 | B1 | 6/2001 | Chin Gan et al. |
| 6,306,177 | B1 | 10/2001 | Felt et al. |
| 6,344,058 | B1 | 2/2002 | Ferree |
| 6,352,557 | B1 | 3/2002 | Ferree |
| 6,402,784 | B1 | 6/2002 | Wardlaw |
| 6,648,918 | B2 | 11/2003 | Ferree |
| 6,733,505 | B2 | 5/2004 | Li |

(Continued)

*Primary Examiner* — Si Ming Ku
(74) *Attorney, Agent, or Firm* — The Noblitt Group, PLLC

(57) ABSTRACT

Various embodiments provide systems and methods for repairing or replacing intervertebral discs as a treatment for derangements. Systems and methods may comprise an intervertebral disc implant for deployment into an intervertebral disc space wherein the nucleus has been at least partially evacuated from the deranged intervertebral disc. The intervertebral disc implant may be intraoperatively and postoperatively filled and/or re-filled with a growth matrix. The intervertebral disc implant may be differentially permeable to the growth matrix to provide directional growth and/or diffusion of the growth matrix to restore height to the intervertebral disc space. Systems and methods may further comprise an implant delivery device for deploying the intervertebral disc implant into the intervertebral disc space.

28 Claims, 22 Drawing Sheets

(56) References Cited

U.S. PATENT DOCUMENTS

| | | |
|---|---|---|
| 7,309,359 B2 | 12/2007 | Trieu et al. |
| 7,741,273 B2 | 6/2010 | McKay |
| 7,837,735 B2 * | 11/2010 | Malone .............. A61B 17/7064 623/17.16 |
| 7,951,110 B2 | 5/2011 | Bishop et al. |
| 7,993,666 B2 | 8/2011 | McKay et al. |
| 8,048,081 B2 | 11/2011 | Shaolian et al. |
| 8,142,503 B2 | 3/2012 | Malone |
| 8,357,388 B2 | 1/2013 | McKay |
| 2002/0128718 A1 | 9/2002 | Ferree |
| 2002/0169162 A1 | 11/2002 | Smith et al. |
| 2003/0039689 A1 | 2/2003 | Chen et al. |
| 2003/0199979 A1 * | 10/2003 | McGuckin, Jr. ........ A61B 17/70 623/17.11 |
| 2003/0220692 A1 | 11/2003 | Shapiro et al. |
| 2005/0203206 A1 | 9/2005 | Trieu |
| 2006/0004457 A1 | 1/2006 | Collins et al. |
| 2006/0093646 A1 | 5/2006 | Cima et al. |
| 2006/0247661 A1 | 11/2006 | Richards et al. |
| 2007/0184033 A1 | 8/2007 | Sevrain et al. |
| 2007/0265561 A1 | 11/2007 | Yeung |
| 2008/0045949 A1 | 2/2008 | Hunt et al. |
| 2008/0177309 A1 | 7/2008 | McLeer |
| 2008/0228193 A1 | 9/2008 | Matityahu |
| 2008/0255501 A1 | 10/2008 | Hogendijk et al. |
| 2008/0255664 A1 | 10/2008 | Hogendijk |
| 2009/0130017 A1 | 5/2009 | Allen et al. |
| 2009/0130167 A1 | 5/2009 | Shelton et al. |
| 2009/0263461 A1 | 10/2009 | McKay |
| 2010/0015196 A1 | 1/2010 | Kimble et al. |
| 2010/0111829 A1 | 5/2010 | Drapeau et al. |
| 2010/0285091 A1 | 11/2010 | Sevrain et al. |
| 2011/0004307 A1 * | 1/2011 | Ahn .................. A61F 2/441 623/17.12 |
| 2011/0029094 A1 | 2/2011 | Hogendijk et al. |
| 2011/0125158 A1 | 5/2011 | Diwan et al. |
| 2012/0101577 A1 | 4/2012 | Lee |
| 2012/0142648 A1 | 6/2012 | Biggs et al. |
| 2012/0165871 A1 | 6/2012 | Malone |

* cited by examiner

Figure 6C:
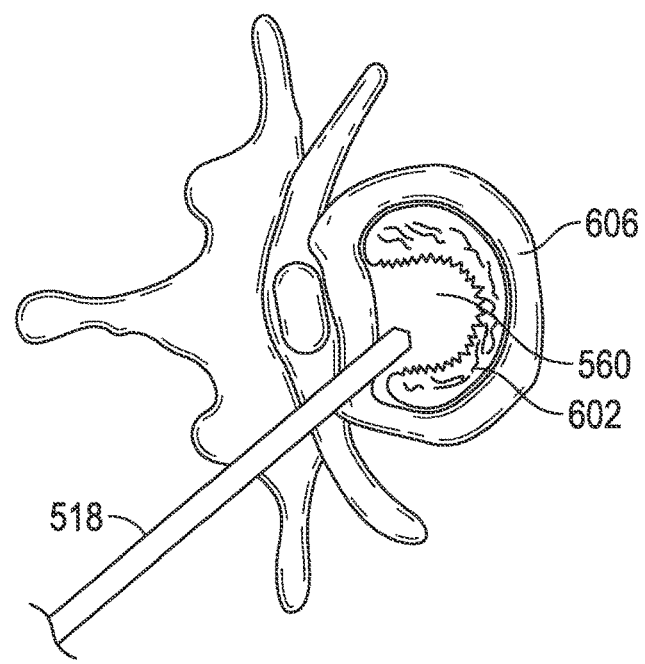
Figure 6D:
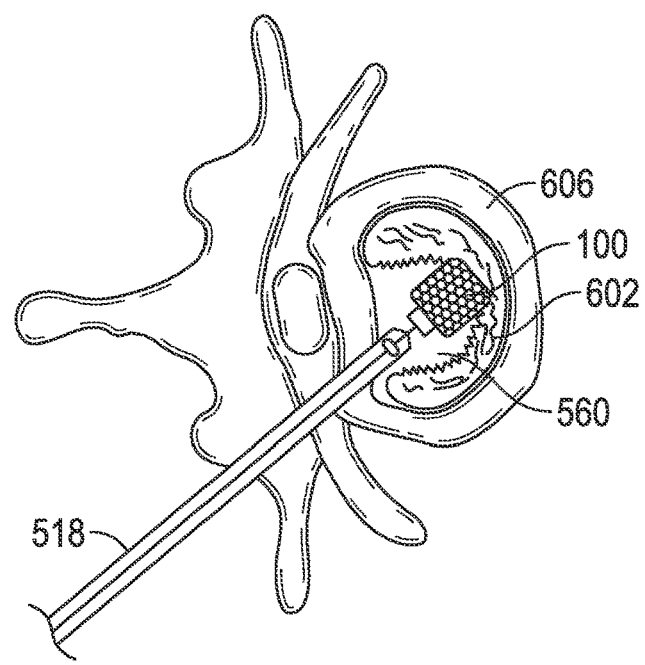
Figure 6E:
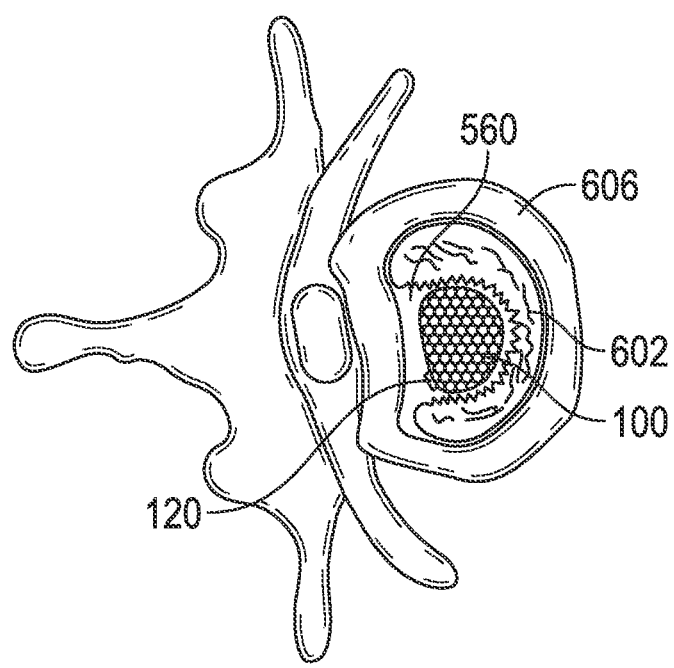

FIG. 6
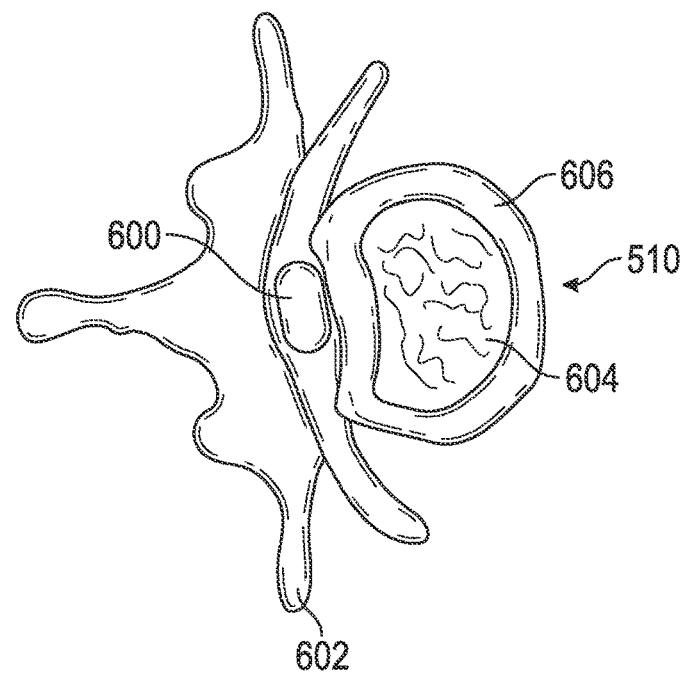
FIG. 6A
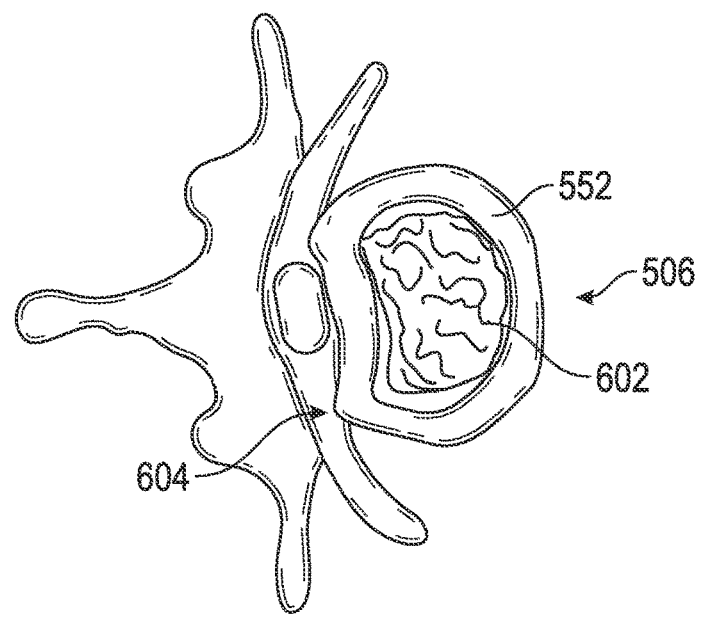
FIG. 6B

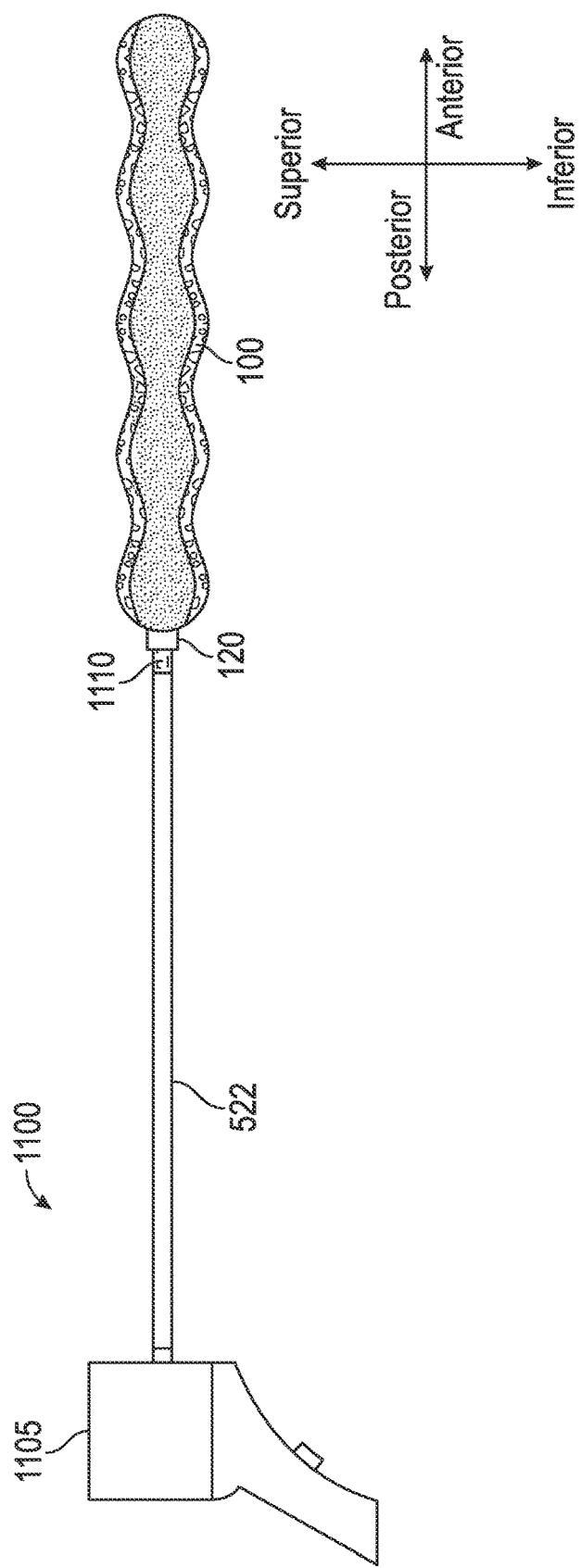

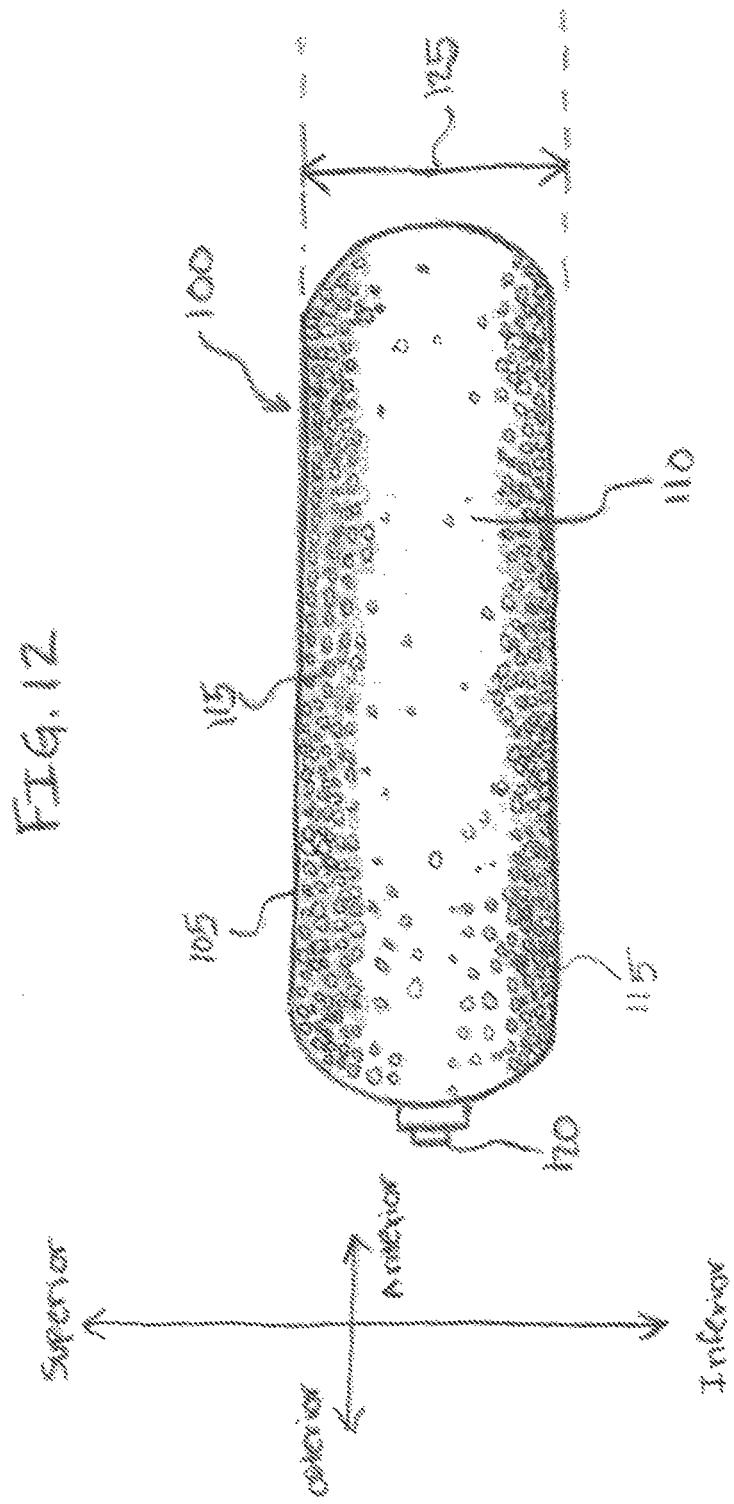

SYSTEMS AND METHODS FOR TREATMENT OF INTERVERTEBRAL DISC DERANGEMENTS

BACKGROUND

Intervertebral discs comprise a highly organized matrix of collagen, water, and proteoglycans produced by differentiated chondrocytes. Each intervertebral discs comprises a central highly hydrated and gelatinous nucleus pulposus (nucleus) surrounded by an elastic and highly fibrous annulus fibrosus (annulus). Cartilaginous endplates provide a connection to the vertebrae inferiorly and superiorly to the intervertebral disc. This cushioned arrangement within the intervertebral discs allows the discs to facilitate movement and flexibility within the spine while dissipating hydraulic pressure through the spine.

Intervertebral discs are susceptible to a variety of derangements from degenerative disease and traumatic injury that may result in molecular and morphological changes that affect the macromolecular structure of the disc. These derangements may cause an at least partial collapse and a loss of height of the intervertebral disc with consequent compression of spinal nerves and pain. For example, degenerative disc disease may occur as an age-related process in which the nucleus changes from a gelatinous material with high water content to a more fibrous, water-depleted material that may form fissures and/or tears. The degenerated nucleus may exhibit a decreased ability to evenly distribute hydraulic pressure from the compression of the spine through the intervertebral disc and may prolapse into the surrounding annulus. Degenerative disc disease may also result in tearing of the vertebral endplates and/or the annulus tissue, causing the nucleus to herniate through the fibers of the annulus to compress spinal nerve roots and cause pain.

Derangements of the intervertebral disc may cause severe back pain, spasms of back muscles, muscle weakness in the legs, numbness in the leg and/or foot, radiating pain down the leg, and changes in bladder and/or bowel function. Pain from intervertebral disc derangements may be intractable and debilitating. Pain may be improved for some patients with physical therapy, modification of activity, and/or medication. Patients that fail to respond to noninvasive interventions for back pain, however, may require surgery on the damaged intervertebral disc.

A variety of surgical interventions may be employed to relieve nerve pressure and pain. For example, one possible treatment may comprise a discectomy wherein a herniated portion of the intervertebral disc is removed. In another procedure, a laminectomy may be performed to remove a portion of the lamina to enlarge the spinal canal and relieve nerve pressure. In a spinal fusion procedure, two or more vertebrae may be permanently fused in the area of the damaged disc to eliminate compression of the damaged disc caused by motion.

Surgical intervention for intervertebral disc derangements may also comprise replacing the damaged disc with an artificial disc in an arthroplasty surgery. Arthroplasty may be preferred to a spinal fusion procedure in some patients because the artificial disc is intended to restore and preserve the native biomechanics of the intervertebral disc, such as providing the requisite cushion to the adjacent vertebra, supporting unrestricted motion of the spine, and reducing or preventing the degeneration of adjacent intervertebral discs, which may be damaged after fusion surgeries due to the permanently altered motion characteristics of the spine in the fused area.

An artificial disc may comprise a variety of biocompatible materials. For example, one type of artificial disc comprises a sliding polyethylene core sandwiched between cobalt chromium alloy endplates. Adverse complications associated with artificial discs include disc migration causing nerve compression which requires revision surgery, degeneration of discs at another level of the spine, subsidence of the artificial discs, facet joint arthrosis, and wear of the polyethylene in the artificial disc. Measures to correct these problems may require a subsequent surgery for removal of the artificial disc and fusion of the affected vertebrae.

BRIEF SUMMARY

Various embodiments provide systems and methods for repairing or replacing intervertebral discs as a treatment for derangements. Systems and methods may comprise an intervertebral disc implant for deployment into an intervertebral disc space wherein the nucleus has been at least partially evacuated from the deranged intervertebral disc. The intervertebral disc implant may be capable of intraoperative and postoperative filling and/or re-filling with a growth matrix. Various regions of the intervertebral disc implant may be differentially permeable to the growth matrix to provide directional growth and/or diffusion of the growth matrix to restore height to the intervertebral disc space. Systems and methods may further comprise an implant delivery device for deploying the intervertebral disc implant into the intervertebral disc space.

BRIEF DESCRIPTION OF THE DRAWING FIGURES

A more complete understanding of the present technology may be derived by referring to the detailed description when considered in connection with the following illustrative figures. In the following figures, like reference numbers refer to similar elements and steps throughout the figures.

Elements and steps in the figures are illustrated for simplicity and clarity and have not necessarily been rendered according to any particular sequence or scale. For example, steps that may be performed concurrently or in different order are illustrated in the figures to help to improve understanding of embodiments of the present technology.

Figure 1A:
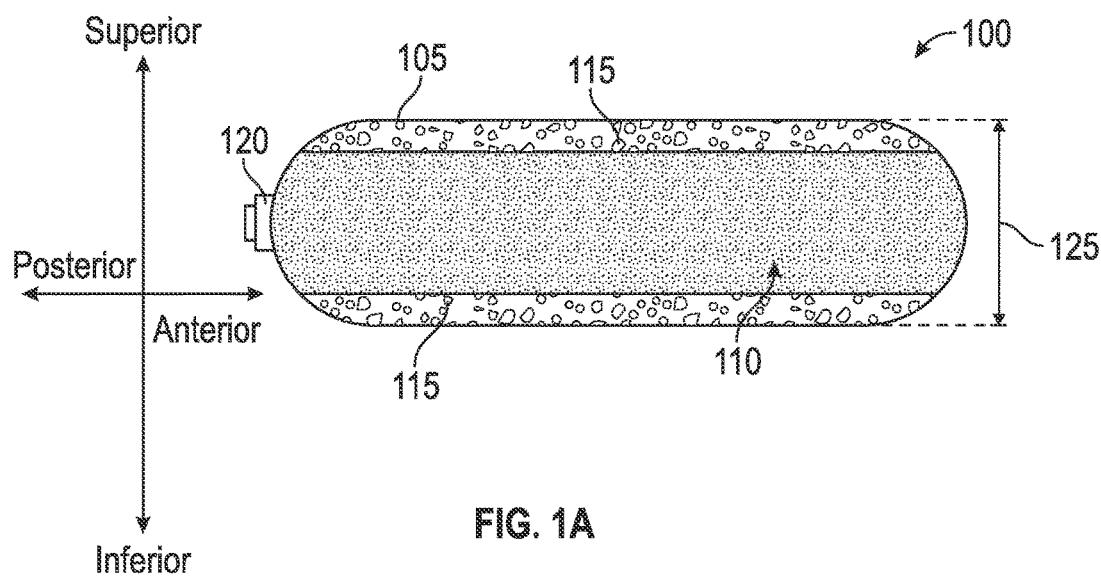
Figure 1B:
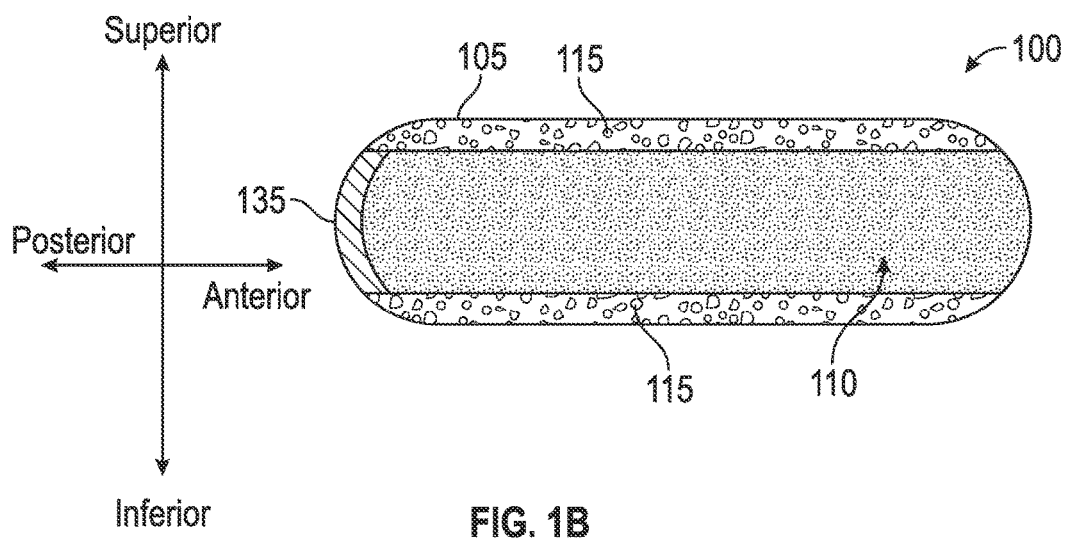
Figure 2:
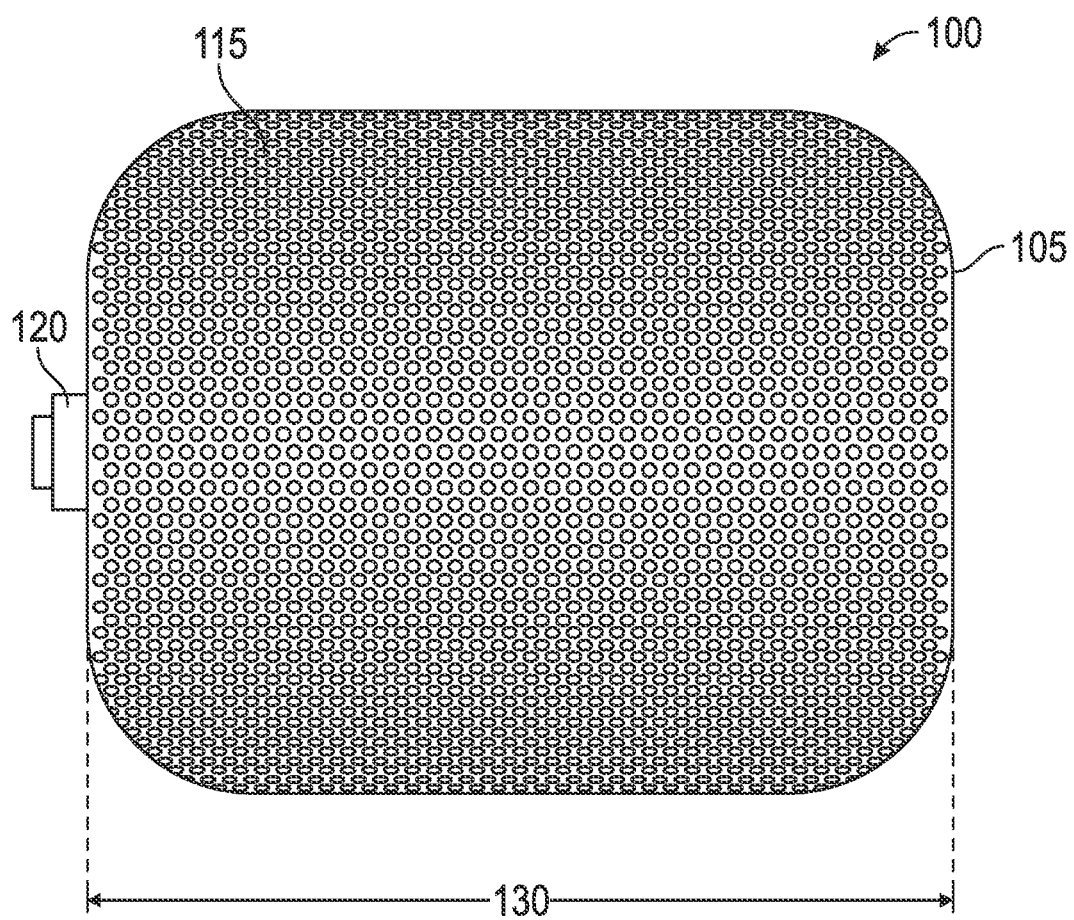
Figure 3A:
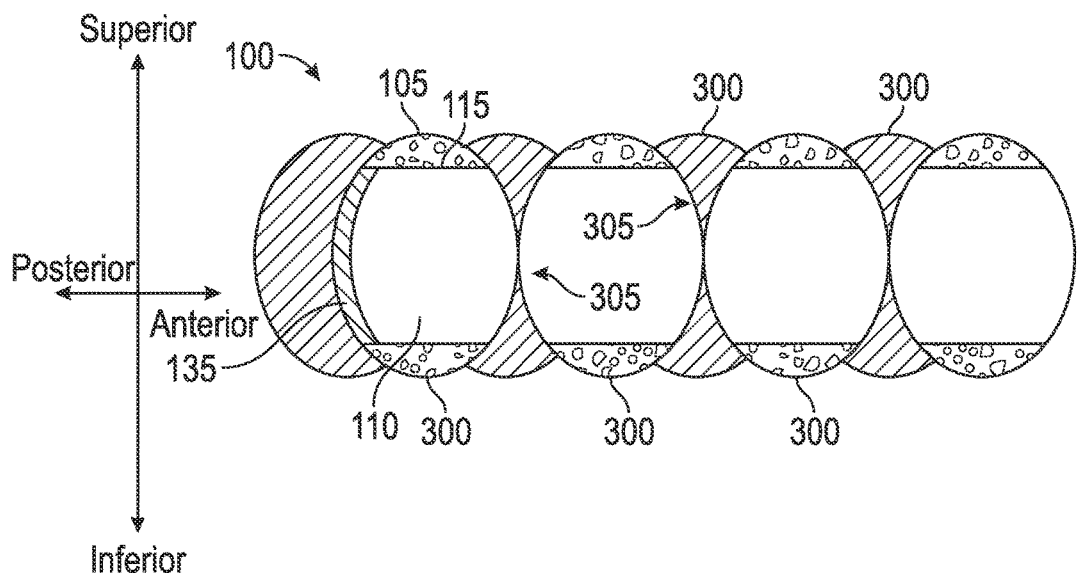
Figure 3B:
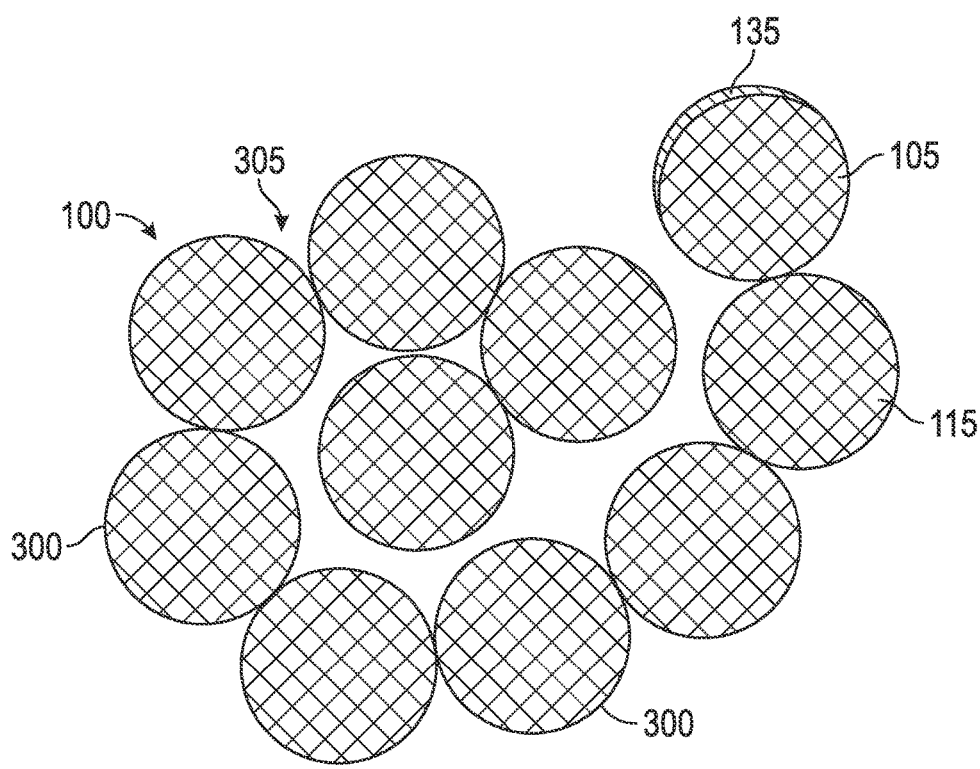
Figure 4:
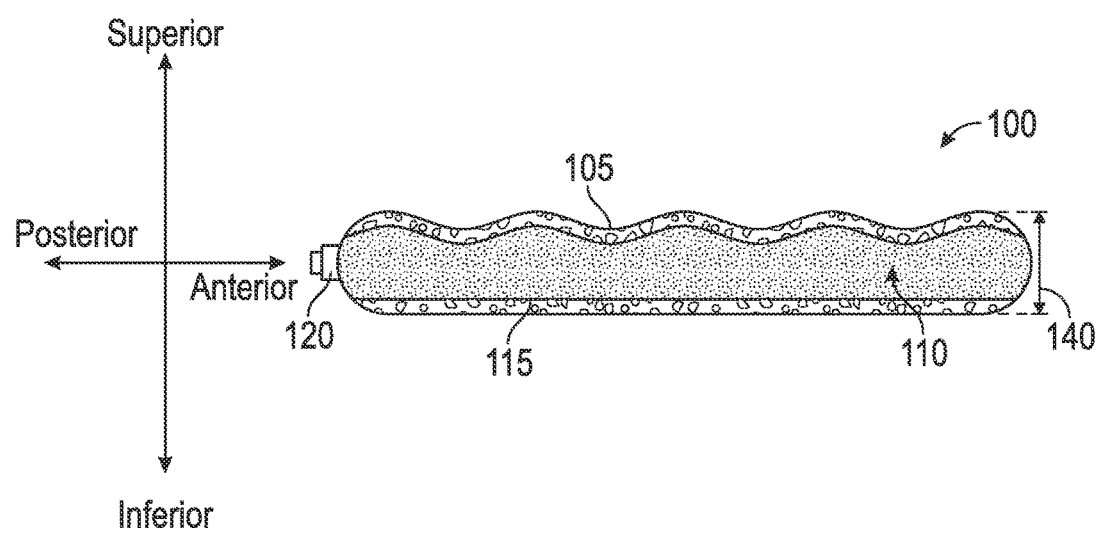
Figure 9:
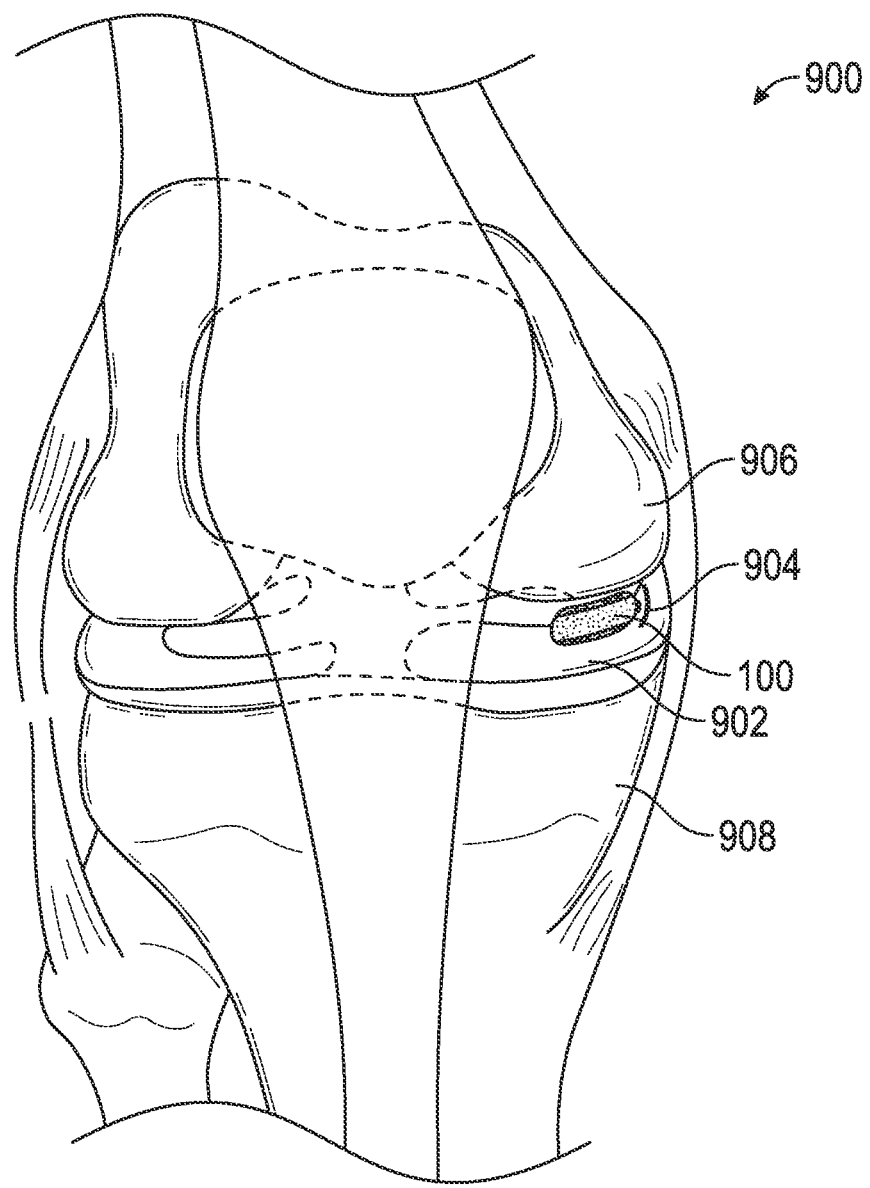
Figure 10:
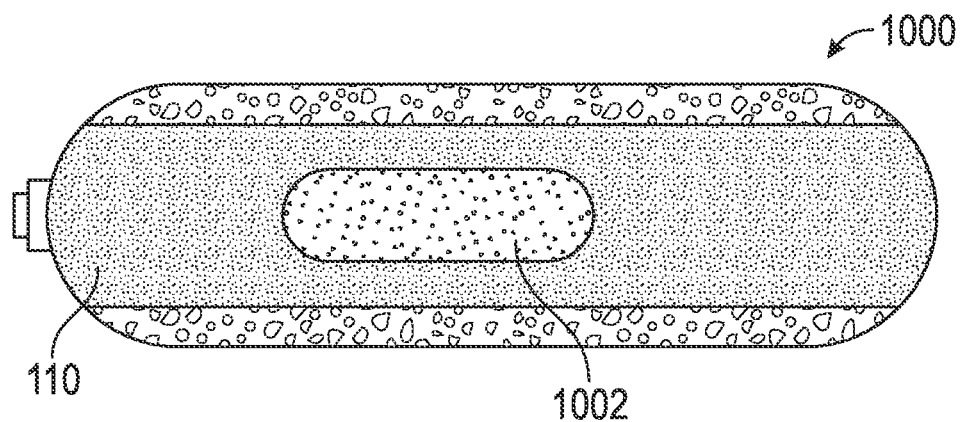
Figure 11B:
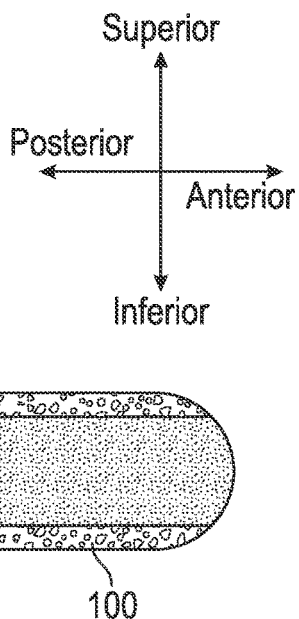
Figure 11C:
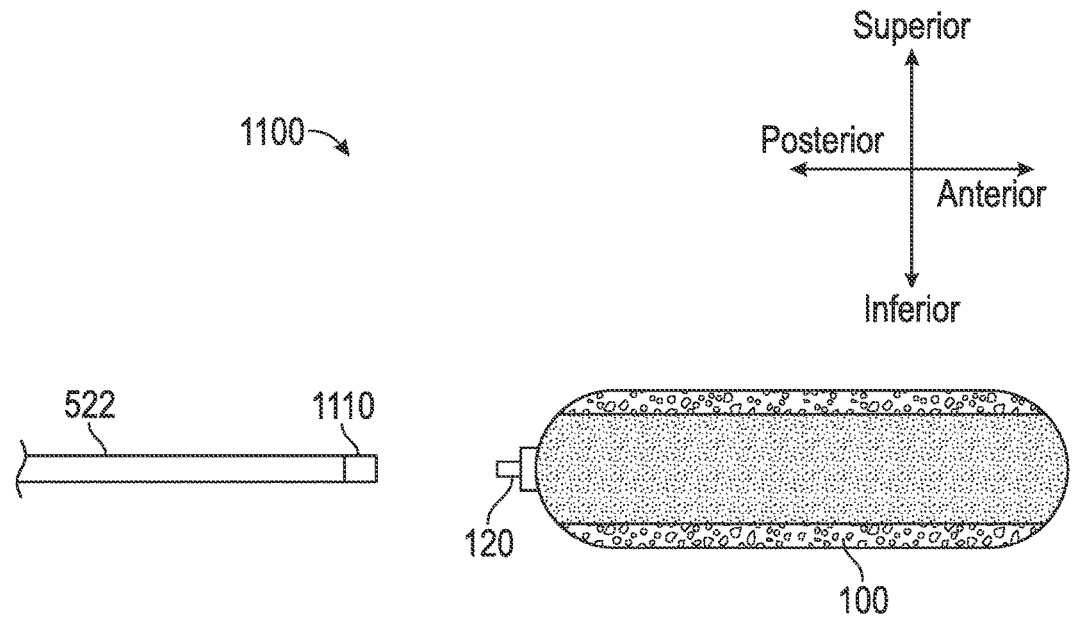

The figures described are for illustration purposes only and are not intended to limit the scope of the present disclosure in any way. Various aspects of the present technology may be more fully understood from the detailed description and the accompanying drawing figures, wherein:

FIGS. 1A-1B representatively illustrate side views of exemplary inflated intervertebral disc implants;

FIG. 2 representatively illustrates a superior (top) view of an exemplary intervertebral disc implant;

FIGS. 3A-3B representatively illustrate a side and superior view, respectively, of an exemplary spiral-form intervertebral disc implant;

FIG. 4 representatively illustrates a side view of an exemplary intervertebral disc implant in a deflated state;

FIGS. 5A-J representatively illustrate an exemplary method for deploying an intervertebral disc implant into an intervertebral disc space comprising a deranged intervertebral disc;

FIGS. 6A-E representatively illustrate an exemplary method for deploying an intervertebral disc implant into an intervertebral disc space;

FIGS. 7A-E representatively illustrate an exemplary method for restoring height to the intervertebral disc space prior to deployment of an intervertebral disc implant;

FIGS. 8A-D representatively illustrate a method for implanting a spiral-form intervertebral disc implant into an intervertebral disc space comprising a deranged intervertebral disc;

FIG. 9 representatively illustrates an exemplary intervertebral disc implant deployed into a knee joint;

FIG. 10 representatively illustrates a side view of an exemplary intervertebral disc implant comprising a nutrient capsule;

FIGS. 11A-C representatively illustrate an exemplary delivery device for deploying an intervertebral disc implant into an intervertebral disc space. and FIG. 12 representatively illustrates a side view of an exemplary intervertebral disc implant with pores distributed in a gradient.

DETAILED DESCRIPTION OF EXEMPLARY EMBODIMENTS

The present technology may be described in terms of functional block components and various processing steps. Such functional blocks may be realized by any number of components configured to perform the specified functions and achieve the various results. For example, the present technology may employ various materials, fill material, growth media, delivery and/or deployment systems, etc. In addition, the present technology may be practiced in conjunction with any number of systems and methods for intervertebral disc repair and/or replacement, and the system described is merely one exemplary application for the invention.

The particular implementations shown and described are illustrative of the invention and its best mode and are not intended to otherwise limit the scope of the present technology in any way. For the sake of brevity, conventional manufacturing, connection, preparation, sterilization, and other functional aspects of the system may not be described in detail. Furthermore, the connecting lines shown in the various figures are intended to represent exemplary functional relationships and/or steps between the various elements. Many alternative or additional functional relationships or physical connections may be present in a practical system.

Various embodiments of the invention provide methods, apparatus, and systems for making an intervertebral disc implant, including an intradiscal implant, and a delivery device for surgical deployment of the intervertebral disc implant into an intervertebral disc space, such as within a partially excised intervertebral disc or in a fully or partially evacuated disc space. A detailed description of various embodiments is provided as a specific enabling disclosure that may be generalized to any application of the disclosed systems and methods in accordance with the various described embodiments.

Various representative implementations of the present technology may be applied to any system for intervertebral disc repair, healing, and/or replacement. Certain representative implementations may include, for example, providing any suitable system or method for restoring height to a compressed intervertebral disc space. In some embodiments, the system or method may comprise an intervertebral disc implant system. For example, intervertebral disc implant 100 may comprise an intradiscal implant for deployment into the intervertebral disc space. At the time of deployment, the intervertebral disc space may contain a degenerated intervertebral disc, a partially evacuated intervertebral disc such as where the nucleus pulposus has been surgically removed, and/or an empty intervertebral disc space wherein the intervertebral disc has been removed.

In various embodiments, the intervertebral disc implant may comprise an expandable pouch. The expandable pouch may comprise a pouch wall defining a lumen. The pouch wall may further comprise a delivery system, such as a plurality of pores, that may allow one or more components of a fill material, such as a growth matrix, disposed within the lumen to permeate and be delivered into the intervertebral disc space. In some embodiments, the expandable pouch may function as a scaffolding in the formation of a structure in an expanding growth matrix. In various embodiments, differences in the location, size, and/or chemical structure of the pores may provide directional permeation of the fill material into the intervertebral disc space. In some embodiments, the expandable pouch may be configured to be intraoperatively fillable and/or post-operatively refillable with the fill material after deployment of the intervertebral disc implant into the intervertebral disc space. The directional movement of the fill material out of the expandable pouch may increase the height of the intervertebral space.

In some embodiments, the intervertebral disc implant system may further comprise a delivery device for deploying the intervertebral disc implant into the intervertebral disc space. In some embodiments, the delivery device may house and/or be coupled to the intervertebral disc implant. In various embodiments, the delivery device may deploy the intervertebral disc implant into the intervertebral disc space, such as through a trocar during surgery.

Referring to FIGS. 1A-B, exemplary embodiments of the intervertebral disc implant 100 may comprise a deformable pouch configured to be inserted into the intervertebral space, such as an expandable pouch 105. The expandable pouch 105 may comprise a fill port, such as a valve 120 and/or a fill diaphragm 135, like a self-sealing septum. The fill port facilitates filling the expandable pouch 105 with a fill material. In some embodiments, the fill port may provide postoperative access to the lumen of the expandable pouch for refilling with the fill material. In one embodiment, the fill port is disposed through a posterior surface of the expandable pouch 105 and configured to provide access to a lumen 110 (the interior cavity) of the expandable pouch 105. In various embodiments, the expandable pouch 105 may be filled with the fill material, such as the growth matrix or other fill material, through the valve 120, such as by connection of the valve to access tubing (not shown).

In another embodiment, the expandable pouch 105 may be filled with the fill material through the fill diaphragm 135, such as by being pierced with a needle intraoperatively. In some embodiments, the expandable pouch 105 may be post-operatively re-filled, such as through a percutaneous procedure in which access to the intervertebral disc implant 100 may be achieved through needle-puncture of the skin. The expandable pouch 105 may have an inflated height 125 that may vary according to the degree the expandable pouch 105 is filled with the fill material.

Referring to FIG. 4, the expandable pouch 105 may have a collapsed height 140. The collapsed height 140 may be shorter than the inflated height 125 to enable transit of the intervertebral disc implant 100 through surgical instruments and/or an access opening surgically created in the compressed intervertebral disc space. The expandable pouch 105 may inflate, such as when filled with the fill material. The expandable pouch 105 may be adapted to have a preselected internal volume for filling with fill material or the expandable pouch 105 may comprise a material with an elastic quality to allow over-distention with the fill material.

Referring to FIGS. 3A-B, the intervertebral disc implant 100 may be configured for ease of insertion and deployment, such as in a spiral form (as shown in the superior view in FIG. 3A). In some embodiments of the spiral-form intervertebral disc implant 100, the expandable pouch 105 may comprise a plurality of interconnected chambers 300. The interconnected chambers 300 may comprise a single, continuous piece of the expandable pouch 105. The interconnected chambers 300 may also comprise separate coupled segments of the expandable pouch 105. In both the continuous and segmented embodiments of the expandable pouch 105, each chamber 300 may comprise a connection area 305 between each adjacent chamber 300. The connection area 305 may comprise any opening, pore, membrane, connector, channel, or the like that may provide fluid communication between the chambers 300. The fill material may enter the fill port and propagate throughout the chambers 300. In one embodiment, the expandable pouch 105 may comprise a self-assembling modular material wherein the chambers 300 assume the spiral-form upon delivery into the intervertebral disc space.

Figure 8A:
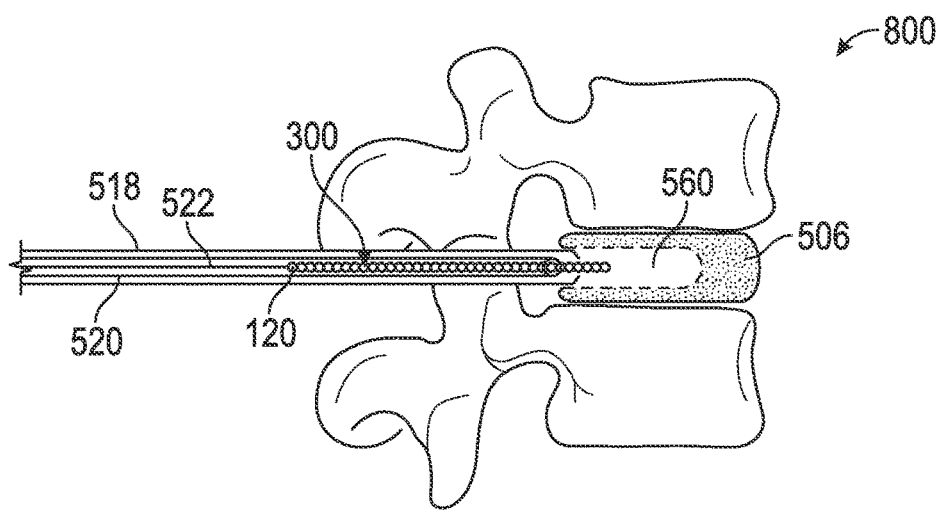
Figure 8B:
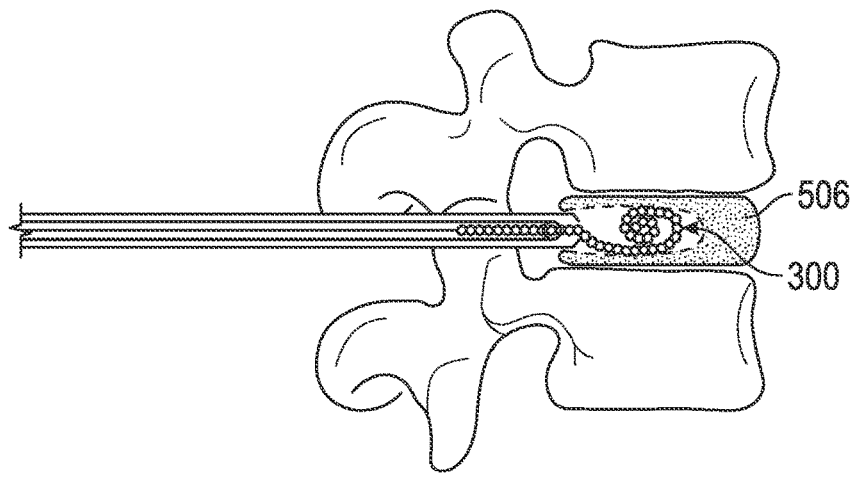
Figure 8C:
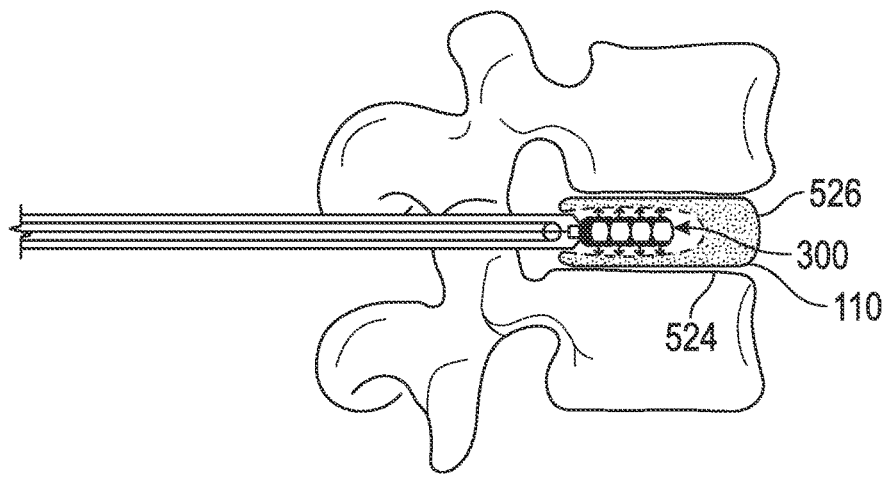
Figure 8D:
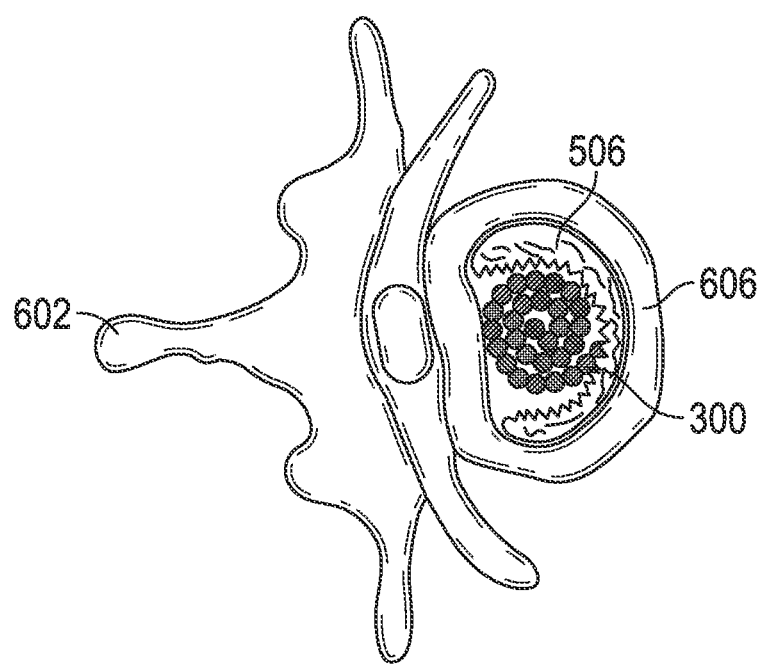

In an exemplary embodiment of the present technology, as shown in the surgical delivery method illustrated in FIGS. 8A-D, the chambers 300 may comprise a linear configuration as the intervertebral disc implant 100 travels through a trocar-cannula 518 (FIG. 8A). The chambers 300 may organize into the spiral configuration upon delivery into an intervertebral disc space 560 (FIG. 8B). Once positioned in the intervertebral disc space 560, the fill material may propagate through and/or grow out of the pores 105 in the intervertebral disc implant 100 (FIG. 8C). As illustrated in the superior view of FIG. 8D, the spiral-form of the intervertebral disc implant 100 may occupy an at least partially empty nucleus space 560.

The expandable pouch 105 may comprise any suitable material for forming an at least partially enclosed balloon-like sac. In various embodiments, the expandable pouch 105 may comprise a material that is biocompatible, biodegradable, dissolvable, and/or bioabsorbable material. The expandable pouch 105 may degrade, dissolve, and/or be absorbed by body fluids over time. The dissolution of the expandable pouch 105 may reduce or eliminate explantation or the need for revision surgery that may arise from its migration within the intervertebral disc space.

In various exemplary embodiments, the expandable pouch 105 may comprise a polymer such as polyacrylate, polyvinylidene, polyvinyl chloride copolymer, polyurethane, polystyrene, polyamide, cellulose acetate, cellulose nitrate, polysulfone, polyphosphazene, polyacrylonitrile, poly(acrylonitrile/covinyl chloride), polyglycolic acid (PGA), polylactic acid (PLA), polylactic-co-glycolic acid (PLGA), poly-ε-caprolactone (PCL), polydioxanone (PDO), a polyethylene, poly(glycerol sebacate) (PGS), or a derivative, copolymer or mixture thereof. In some embodiments, the expandable pouch 105 may comprise a biocompatible elastomeric material. In various embodiments, the expandable pouch 105 may comprise a radiopaque material to allow visualization of the intervertebral disc implant 100 using imaging techniques during surgical implantation, post-operative needle insertion into the intervertebral disc implant 100 for refilling with the filling material, and post-operative follow up for positioning of the intervertebral disc implant 100. For example, the radio opaque material may comprise radiopaque thermoplastic compounds, barium sulfate, bismuth, tungsten, and other radiopaque materials or combinations thereof.

In various embodiments of the present technology, the expandable pouch 105 may be configured to transfer material from the pouch 105 to the intervertebral space. For example, the expandable pouch 105 may comprise a delivery system for transferring fill material to the intervertebral space, such as a plurality of pores 115 defined through the pouch 105 material. The pores 115 may be arranged in any suitable manner across the expandable pouch 105 to provide the desired repair and/or replacement of the deranged intervertebral disc.

For example, in some embodiments, the pores 115 may be arranged to direct the permeation of the growth matrix primarily through the superior and/or inferior surfaces of the expandable pouch 105. The superior and/or inferior permeation of the growth matrix into the intervertebral disc space may promote contact of the growth matrix with the superior and inferior endplates adjacent to the deranged intervertebral disc, as opposed to lateral diffusion out of the intervertebral disc space. Contact with the endplates may in turn increase the height of the compressed intervertebral disc space.

In various embodiments, the pores 115 in the expandable pouch 105 may be arranged in any suitable manner that may promote the directional permeation, diffusion, and/or growth of the fill material out of the intervertebral disc implant 100. In various embodiments, the pores 115 may be arranged according to any pore parameters, such as one or more of pore diameter, pore location, pore concentration, and pore lumen chemistry, such as hydrophobicity or hydrophilicity.

Referring to FIG. 12, In some embodiments, the pore parameter may be arranged as a gradient along one or more surfaces of the expandable pouch 105. For example, in one embodiment, the pore parameter may be a density gradient of the pores 115 that may begin with the highest concentration of pores 115 located primarily on the superior and/or inferior surface of the expandable pouch 105 and decrease in concentration toward the lateral sides of the expandable pouch 105. In another embodiment, the pore parameter may be a gradient of the diameter such that pores 115 having a larger diameter may be disposed on the superior and/or inferior surfaces of the expandable pouch 105 and pores 115 having comparatively smaller diameters may be disposed on the lateral surfaces. In another embodiment, a sealant, such as Duraseal®, may be applied to some areas of the pores 115 to create one or more zones of permeability to the fill material and impede others.

In the exemplary embodiments shown in FIGS. 1A and 1B, the pores 115 may be located on a superior and inferior surface of the expandable pouch 105 with an absence of pores 115 along the lateral sides. In one embodiment, as illustrated in FIG. 2, the pores 115 may be distributed substantially evenly across the superior and/or inferior portion of the expandable pouch 105. In other embodiments, the pores 115 may be distributed across the superior and/or inferior portion of the expandable pouch 105 in any suitable pattern, such as a substantially regular pattern (as shown) and/or an irregular pattern (not shown).

In various embodiments of the present technology, strategic placement of the pores 115 on the superior and/or inferior surfaces of the expandable pouch 105 may facilitate the restoration of the height of the intervertebral disc space. For example, the pores may be selectively placed to direct the permeation of the growth matrix toward the vertebral endplates that form the superior and inferior boundaries of the intervertebral disc space. In some embodiments, lateral surfaces of the expandable pouch 105 may be less permeable than at least one of the superior surface and the inferior surface of the expandable pouch 105. In some embodiments, lateral surfaces of the expandable pouch 105 may be substantially impermeable to the growth matrix. In one embodiment, the height of the intervertebral disc space may be improved or restored as components of the growth matrix, such as dividing cells as discussed below, proliferate through the pores 115 and establish a resilient structure on the inferior and/or superior surfaces of the adjacent vertebrae.

In various embodiments of the present technology, the directional permeability of the intervertebral disc implant 100 may promote an increase in the height of the intervertebral disc space without substantial changes in its width and/or depth. For example, deployment of the intervertebral disc implant 100 into an annulus where the nucleus, or portion thereof, has been removed may result in a natural border for the intervertebral disc implant 100. The natural border may comprise the inferior endplate of the superior vertebra, the superior endplate of the inferior vertebra, and the lateral borders of the annulus. Filling and distension of the expandable pouch 105 with the growth matrix and subsequent permeation, diffusion, and/or growth of the growth matrix may be substantially confined by these natural borders. The embodiments of the expandable pouch 105 wherein the distribution of the pores 115 provide permeability across at least one of the superior surface and the inferior surface of the expandable pouch 105 and comparatively less permeability across the lateral surfaces of the expandable pouch 105 may further promote the restoration of height of the intervertebral disc space. As a result, the directional permeability provided by the arrangement of the pores 115 in the expandable pouch 105 may increase the height of the intervertebral disc without a detrimental increase in disc circumference.

The pores 115 may be created in the expandable pouch 105 through any suitable process. In some embodiments, expandable pouch 105 may be created in a mold defining pores, such as a mold used during curing of the expandable pouch 105. In one embodiment, the pores 115 may be created with conventional stamping methods, compression of large pores into comparatively smaller pores of a desired diameter, chemical etching, and/or bombardment methods such as laser irradiation and/or ion irradiation. In various embodiments, the pores 115 may be created on a nanometric to micrometric scale. For example, the pores 115 may have a diameter of approximately 10 µm to promote diffusion and/or growth of the growth matrix through the pores 115.

Referring again to FIGS. 1A and 1B, in various embodiments of the present technology, the height 125 of the intervertebral disc implant 100 in a fully inflated state may be approximately the desired height of an intervertebral disc space between two adjacent vertebrae. Additionally, the length 130 of the intervertebral disc implant 100 in a fully inflated state may be approximately the length of the intervertebral disc. Accordingly, the intervertebral disc implant 100 may be provided in a variety of heights 125, lengths 130, and other configuration aspects to accommodate variations between patients. For example, a particular size of intervertebral disc implant 100 may be used for patients based on gender, height, age, and/or ethnicity. The location of the damaged intervertebral disc in the low lumbar, higher lumbar, thoracic, or cervical spine may also influence the configuration of the intervertebral disc implant 100.

The desired height 125, width, and/or length 130 of the intervertebral disc implant 100 may be determined intraoperatively by a surgeon based on the patient's anatomy using imaging information, such as computed tomography (CT) imaging information or other imaging studies, of the patient's vertebrae and intervertebral discs. For example, in one exemplary embodiment, the intervertebral disc implant 100 may be configured to fit in the at least partially evacuated nucleus space of an intervertebral disc. In some embodiments, the inflated intervertebral disc implant may be at least approximately 1 inch long, at least approximately 0.5 inches wide, and at least approximately 0.25 inches in height. In some embodiments, the inflated intervertebral disc implant 100 may be may be approximately up to 2 inches long by up to 1.5 inches wide by up to 0.5 inches in height to fit into the at least partially evacuated nucleus space. In some embodiments, the inflated intervertebral disc implant 100 may be approximately 1-2 inches long, 0.5-1 inches wide, and/or 0.25-0.5 inches in height.

Based upon the surgeon's intraoperative assessment of the volume of the at least partially evacuated nucleus space, a fill volume for the expandable pouch 105 may be selected. The intervertebral disc implant 100 may be filled with the fill material up to a maximum fill volume resulting in the height 125 or may be underfilled to an amount less than the maximum fill volume to accommodate differences in the intervertebral disc space in different patients or within the vertebrae of the same patient. For example, in one embodiment, the intervertebral disc implant 100 may be filled within a range of approximately 0.5 cc to 5 cc of fill material.

Referring to FIG. 4, an empty intervertebral disc implant 100 may be in an at least partially collapsed state and may have a height 140 that may be shorter than the height 125 of an at least partially to fully inflated intervertebral disc implant 100. In one embodiment, the height 140 may be adapted to allow the intervertebral disc implant 100 to fit through an inner opening of a trocar-cannula tool for surgical implantation. For example, the intervertebral disc implant 100 may fit through the trocar-cannula wherein the diameter of the inner opening is less than approximately 20 millimeters. In some embodiments, the diameter of the trocar-cannula's inner opening may be approximately 5 millimeters or less. In various embodiments, the height of the deflated intervertebral disc implant 100 may be equal to or less than the diameter of the inner opening of the trocar-cannula used to surgically introduce the intervertebral disc implant 100 into the intervertebral disc space. In various embodiments of the present technology, the intervertebral disc implant 100 may be filled with the fill material through a fill port, such as a valve 120 or a fill diaphragm 135. The fill port may be located on any suitable surface of the intervertebral disc implant 100 such that the fill material may be inserted into the lumen 110, such as injection after implantation into the intervertebral disc space. In one embodiment, the fill port may be a discrete injection site on a posterior-lateral or side surface of the intervertebral disc implant 100 to orient the injection site. Such orientation may facilitate intra-operative filling and/or post-surgical re-filling of the intervertebral disc implant 100. In some embodiments, the fill port may include the fill diaphragm 135 comprising a suitable biocompatible self-sealing injection material, such as rubber or silicone. In another embodiment, the fill port may comprise the valve 120 or other device that may be connected to a fill tube (not shown).

In various embodiments of the present technology, the intervertebral disc implant 100 may be placed into the intervertebral disc space using a delivery device. For example, the delivery device may comprise a suitable rod or cannula that may be coupled to and/or at least partially house the intervertebral disc implant 100. The delivery device may be coupled to the intervertebral disc implant 100 with any suitable connector, such as a snap, adhesive, clamp, clip, and the like that may be mechanically uncoupled (such as with a twist and/or pop of the delivery device to dissociate from the intervertebral disc implant 100) and/or chemically uncoupled after implantation of the intervertebral disc implant 100 into the intervertebral disc space. In some embodiments, the delivery device may comprise a tube or needle configured to fill the intervertebral disc implant 100 with the fill material during and/or after deployment of the intervertebral disc implant 100 into the intervertebral disc space. In various embodiments, the delivery device may be configured to pass through the trocar-cannula, implant the intervertebral disc implant 100 into the intervertebral space, uncouple from the intervertebral disc implant 100, withdraw from the intervertebral space, and be removed from the trocar-cannula.

Referring to FIGS. 11A-C, an exemplary delivery device 1100 may comprise an introducer tool 1105. The introducer tool 1105 may comprise a handle configured to be coupled to a delivery cannula 522. The introducer tool 1105 may be used to push the delivery cannula 522 through the trocar-cannula (not shown) and into the intervertebral disc space. The introducer tool 1105 and delivery cannula 522 of the delivery device 1100 may be configured to travel through a trocar to reach the intervertebral disc space having a diameter that is equal to or smaller than the inner diameter of the trocar-cannula, such as less than 20 millimeters in diameter. The introducer tool 1105 may comprise any suitable mechanism, such as a switch, trigger, button, or release for the surgeon to control the attachment of the delivery cannula 522 to the intervertebral disc implant 100.

For example, in one embodiment, the delivery cannula 522 may comprise a fastener 1110 that may be coupled to the valve 120 for positioning the intervertebral disc implant 100 in the intervertebral space. The fastener 1110 may dissociate from the valve 120, as shown in FIG. 11C, leaving the intact intervertebral disc implant 100 behind in the intervertebral space. In some embodiments, as shown in FIG. 11B, the delivery device 1100 may further comprise or be configured to accept a needle 1115 for operating the fill port to fill the intervertebral disc implant 100 with the fill material.

In various embodiments of the present technology, the fill material may include therapeutic materials to be exposed to the surrounding tissue, such as a growth matrix. The growth matrix may comprise any material that may comprise a biological material and/or any material that may support, or augment, regulate, propagate, or otherwise sustain the growth of the biological material. For example, the biological material may comprise cells and/or tissue that may provide restoration of height to the intervertebral disc space as the biological material grows and/or diffuses through the pores 115 of the intervertebral disc implant 100. In various embodiments, the growth matrix may comprise one or more of cells or tissue such as stem cells and/or chondrocytes, cellular matrix materials such as biopolymers or other scaffolding materials, nutritional media, and/or additives such as growth and/or differentiation factors. In one embodiment, the components of the growth matrix comprising cells or tissue, cellular matrix material, and/or additives may be commixed in vitro prior to injection into the intervertebral disc implant 100. In another embodiment, the growth matrix may be aerated with a gas optimized for cell growth prior to injection into the intervertebral disc implant 100. Ultimately, nutrition and gas exchange may be supplied by diffusion from nearby blood vessels to the cells or tissue of the growth matrix.

In some embodiments, the cellular matrix materials may comprise a supportive scaffold structure for the cells and/or tissue to divide and form three-dimensional tissue structures. In one embodiment, the resultant tissue structure may function as a prosthetic intervertebral disc. In various embodiments, some components of the cellular matrix materials may be non-toxic, biocompatible, and/or biodegradable. For example, the cellular matrix material may comprise biodegradable biopolymers including organic polymers such as polyglycolic acid (PGA), polylactic-co-glycolic acid (PLGA), poly-ε-caprolactone (PCL), polyamino acids, polyanhydrides, and/or polyorthoesters. The biodegradeable biopolymers may also comprise natural hydrogels such as collagen, hyaluronic acid, alginate, agarose, and/or chitosan. Additionally, the biodegradeable biopolymers may comprise synthetic hydrogels such as poly(ethylene oxide) (PEO), poly(vinyl alcohol) (PVA), poly(acrylic acid) (PAA), poly (propylene fumarate-co-ethylene glycol) [P(PF-co-EG)], and/or copolymers thereof.

In various embodiments, the growth matrix may comprise any additives needed for propagation of the cells or tissue. For example, the additives may comprise a nutritional medium for supplying a carbohydrate source, supplements, vitamins, minerals, growth factors, differentiation factors, hormones, attachment factors, and/or salts to promote viability of the cells and/or tissue. In some embodiments, the additives including nutritional media may be at least partly a solid, liquid, and/or a gel.

Referring to FIG. 10, in various embodiments of the present technology, the intervertebral disc implant 100 may comprise a nutrient capsule 1002. The nutrient capsule 1002 may comprise one or more additives that are disposed in a controlled release capsule and/or gel system. In one embodiment, the nutrient capsule may be a cellulose derivative polymer such as hydroxypropylmethylcellulose (e.g., Methocel®) wherein the additive wets and hydrates the cellulose and slowly diffuses out of the cellulose into the lumen 110 of the intervertebral disc implant 100. The slow release of the additives may provide additional nutrition and growth factors to support the propagation of the cells and/or tissue after the additives provided in the lumen 110 of the intervertebral disc implant 100 are consumed.

In operation, the intervertebral disc implant 100 may be surgically introduced into the intervertebral disc space using the delivery device inserted through the trocar-cannula. An exemplary method of deploying the intervertebral disc implant 100 into the intervertebral disc space is illustrated in a lateral view shown in FIGS. 5A-J and a superior view shown in FIGS. 6A-E. A portion of a spine 500 may comprise a healthy intervertebral disc 510 that maintains a normal intervertebral disc space height 526 between vertebral body 512 and vertebral body 508, providing spinal flexibility (see FIG. 5A). As shown in FIG. 6A, the healthy intervertebral disc 510 comprises an annulus 606 and a hydrated healthy nucleus 604.

The spine 500 may also comprise a deranged intervertebral disc 506. As illustrated in the superior view shown in FIG. 6B, the deranged intervertebral disc 506 may comprise an annulus 606 and a dehydrated nucleus 602. The deranged intervertebral disc 506 may comprise any number of other derangements including, but not limited to, a protrusion/herniation 604 as shown in FIG. 6B and/or degenerative disc disease that may result in the compression and/or loss of elasticity of the deranged intervertebral disc 506. The deranged intervertebral disc 506 may result in a compressed intervertebral disc space height 528 between vertebral body 502 and vertebral body 512.

Figure 5A:
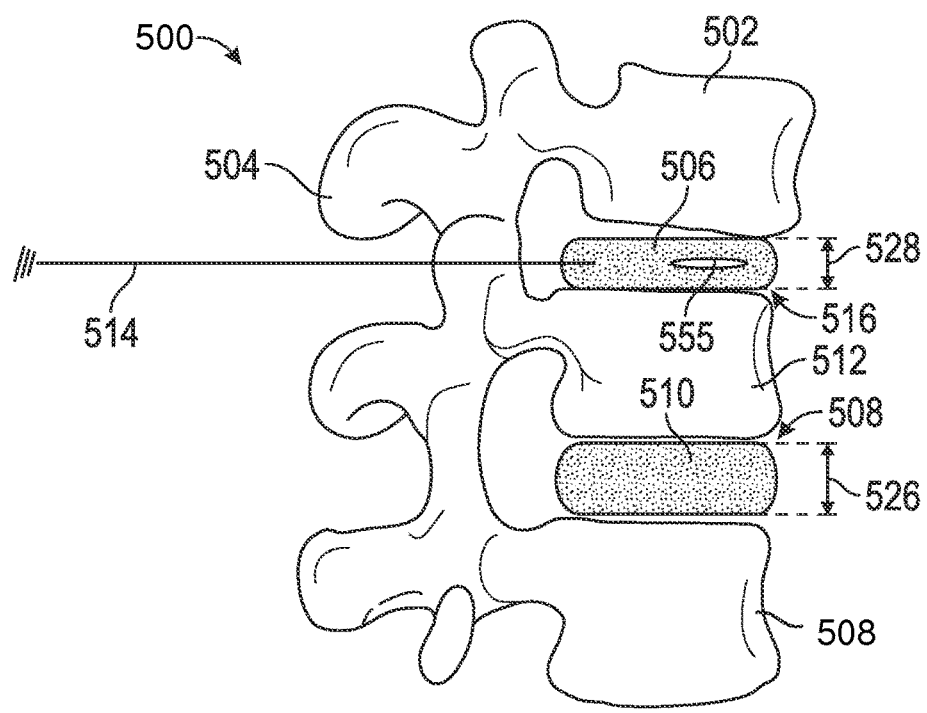
Figure 5B:
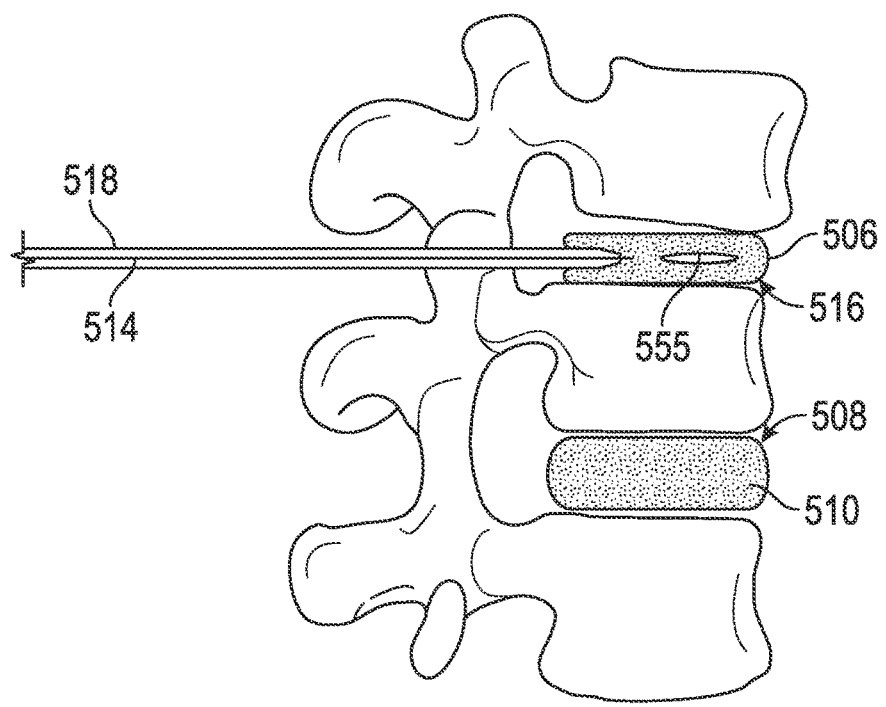

As illustrated in FIGS. 5A-J, the deranged intervertebral disc 506 may comprise an annular tear 555 (FIGS. 5A, 5B). Diffusion and growth of the growth matrix from the intervertebral disc implant 100 deployed into the deranged intervertebral disc 506 may promote at least partial repair of the annular tear 555. At least partial repair of the annular tear 555 may reduce chemical leaks out of the intervertebral disc space 516. Such leaks may irritate nerves (not shown) in the vertebral foramen (600 of FIG. 6A) and cause back pain and/or radicular pain.

Deployment of the intervertebral disc implant 100 into the deranged intervertebral disc 506 to at least partially repair the derangement may be performed in any suitable surgical procedure such as conventional arthroplasty surgery or a transpedicular discectomy. The surgical procedure may be an open procedure, a minimally invasive image-guided procedure (such as fluoroscopically or x-ray guided), or endoscopically as guided by a camera. Generally, a trocar comprising an obturator 514 and a trocar-cannula 518 may provide an access port to the deranged intervertebral disc 506 (FIG. 5B). As shown in FIGS. 5A and 5B and FIGS. 6C-D, the obturator 514 and trocar-cannula 518 may be inserted from a minimally invasive posterior lateral position to access the intervertebral disc 506, bypassing the vertebral foramen 600 (shown in FIGS. 6C and 6D). Access to the deranged intervertebral disc 506 may also be performed in laparoscopic anterior spine surgery through the abdomen or in a lateral fashion with the patient on his or her side which may avoid the major muscles of the back (methods not shown). The trocar-cannula 518 may be slipped over the obturator 514 to provide a hollow access tube that reaches the deranged intervertebral disc 506 (FIG. 5B).

Figure 5C:
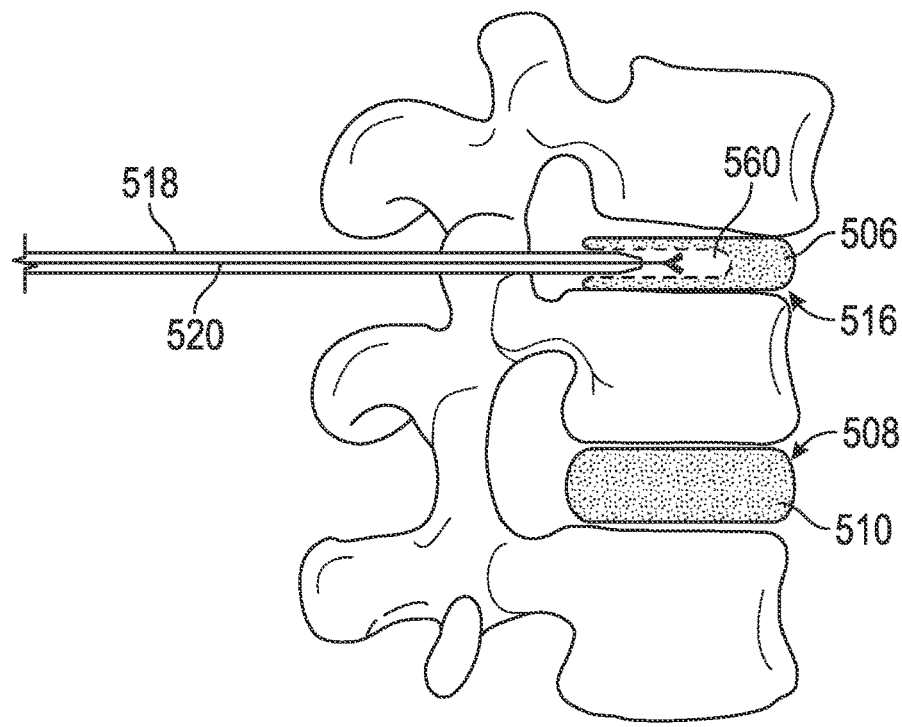
Figure 5D:
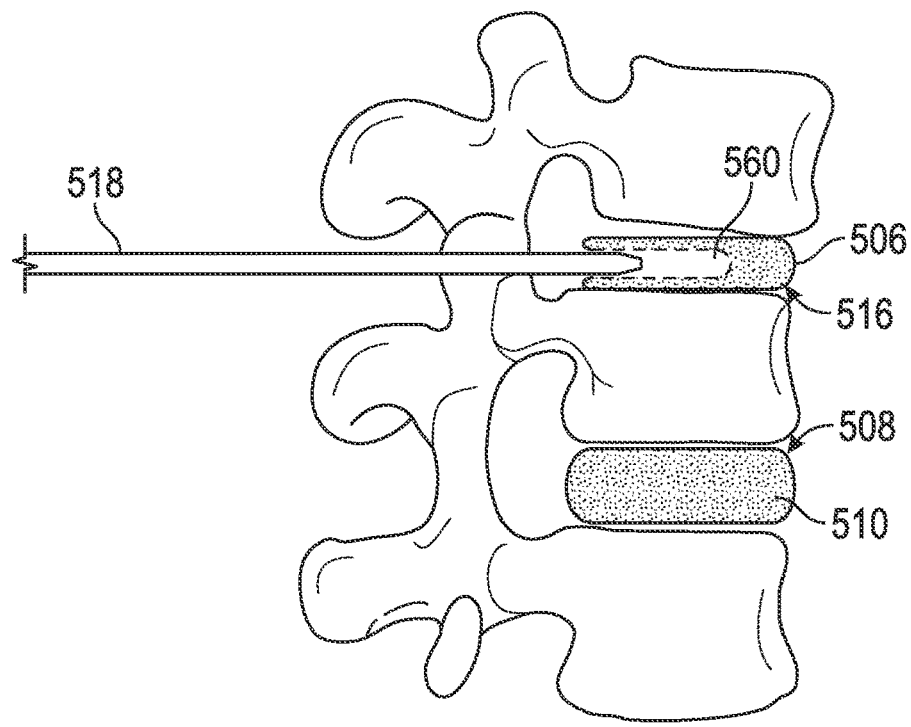

The obturator 514 may be withdrawn and a cutting cannula 520 may be inserted into the trocar-cannula 518 (FIG. 5C). The cutting cannula 520 may at least partially remove the dehydrated nucleus 608 through the trocar-cannula 518 leaving an at least partially empty nucleus space 560 (see FIGS. 5C and 5D, and FIG. 6C). The cutting cannula 520 may then be removed from the trocar-cannula 518 (FIG. 5D).

Figure 5E:
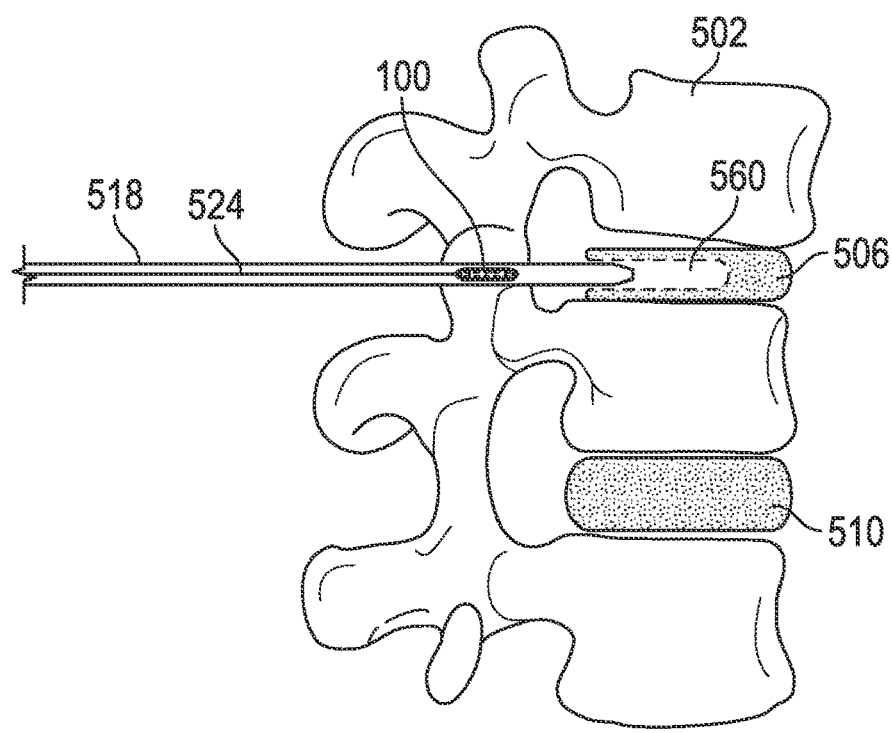
Figure 5F:
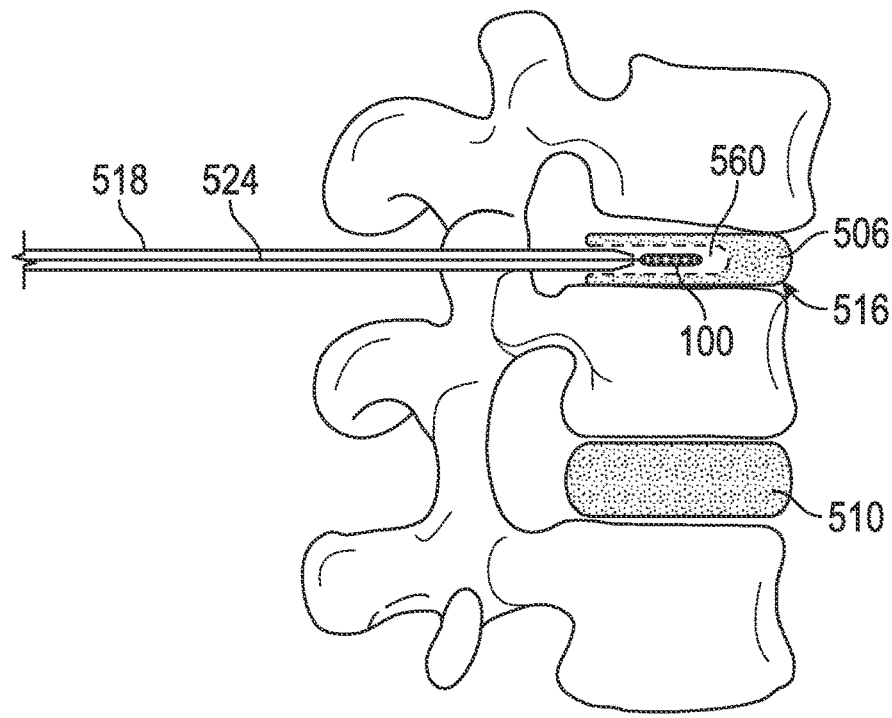
Figure 5G:
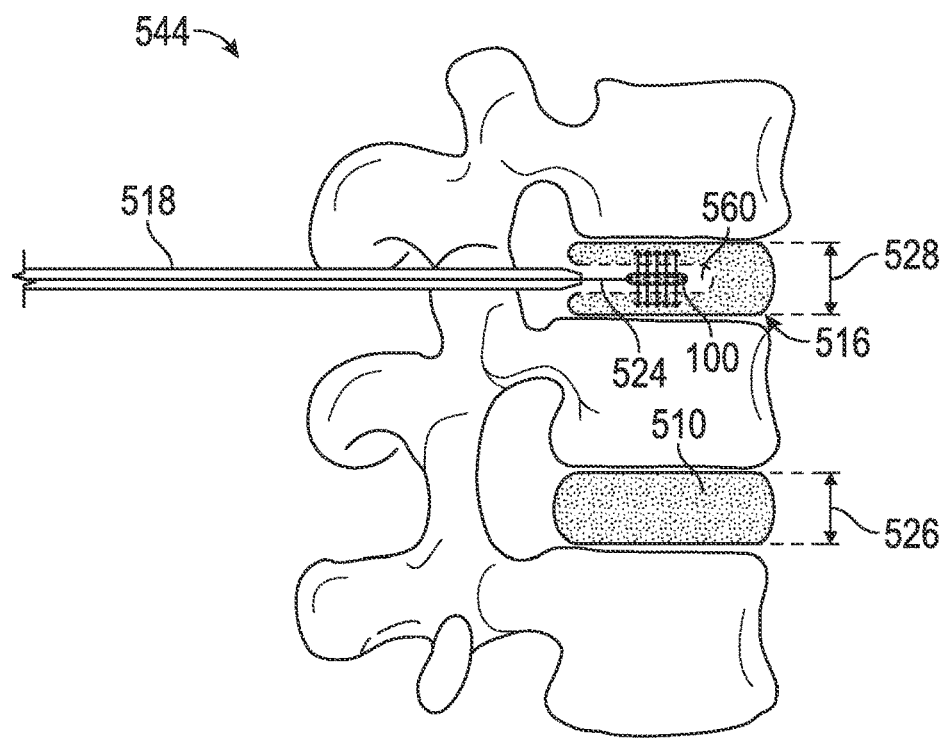

In some embodiments of the method for deploying the intervertebral disc implant 100 into the nucleus space 560, the delivery cannula 524 of the delivery device 1100 may be coupled to the at least partially deflated intervertebral disc implant 100 and inserted into the trocar-cannula 518 (FIG. 5E). The at least partially deflated intervertebral disc implant 100 may be advanced through the trocar-cannula 518 and deployed into the nucleus space 560 (FIG. 5F). Upon placement in the nucleus space 560, the intervertebral disc implant 100 may be filled intraoperatively to a desired volume with the growth matrix, such as through the needle 1115 (not shown) (FIG. 5G).

Figure 5H:
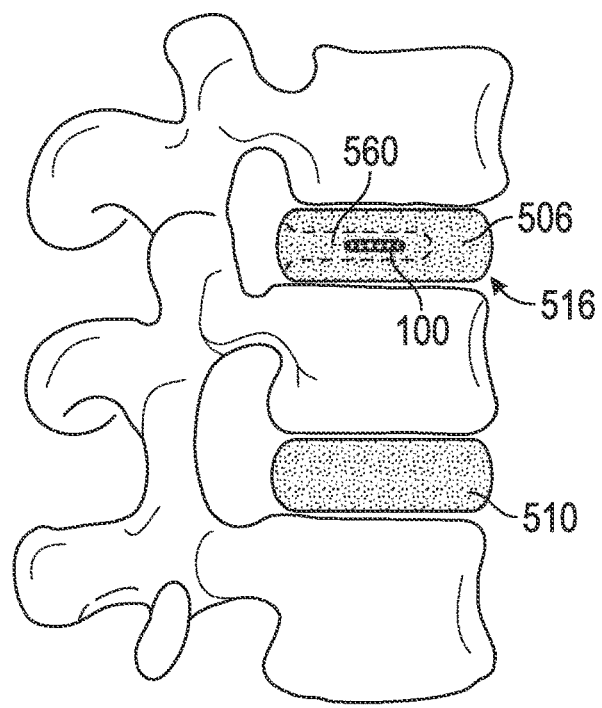
Figure 5I:
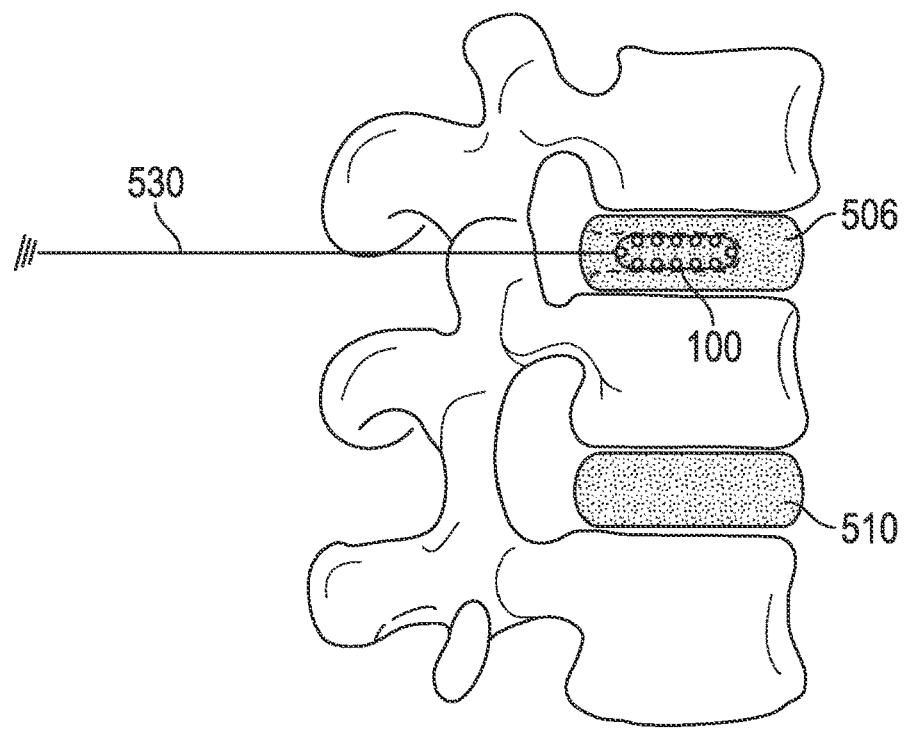

The growth matrix may begin directional diffusion and/or directional growth out of the intervertebral disc implant 100 into the intervertebral disc space 516. As a result, the height 528 of the intervertebral disc space 516 may be intraoperatively and/or gradually postoperatively restored to a height similar to the normal intervertebral disc space height 526, relieving the patient's spinal pain. After successful placement and filling of the intervertebral disc implant 100, the delivery cannula 522 may be uncoupled from the intervertebral disc implant 100 and removed from the trocar-cannula 518 (not shown). Finally, the trocar-cannula 518 may be removed from the intervertebral disc space 516 to end the surgery (FIG. 5H).

Figure 7A:
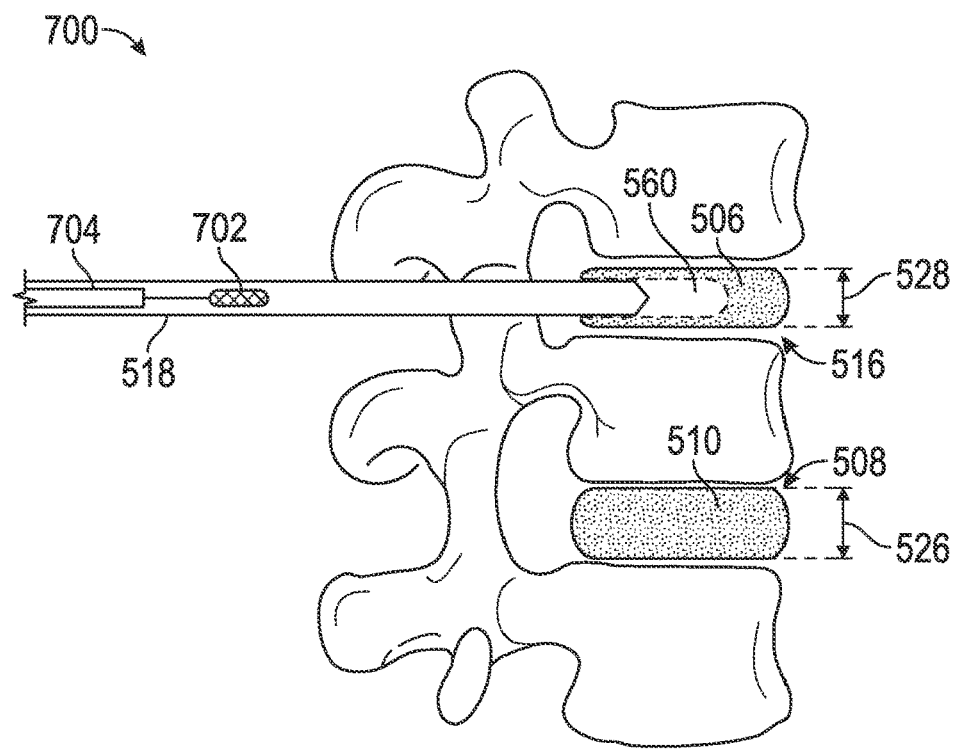
Figure 7B:
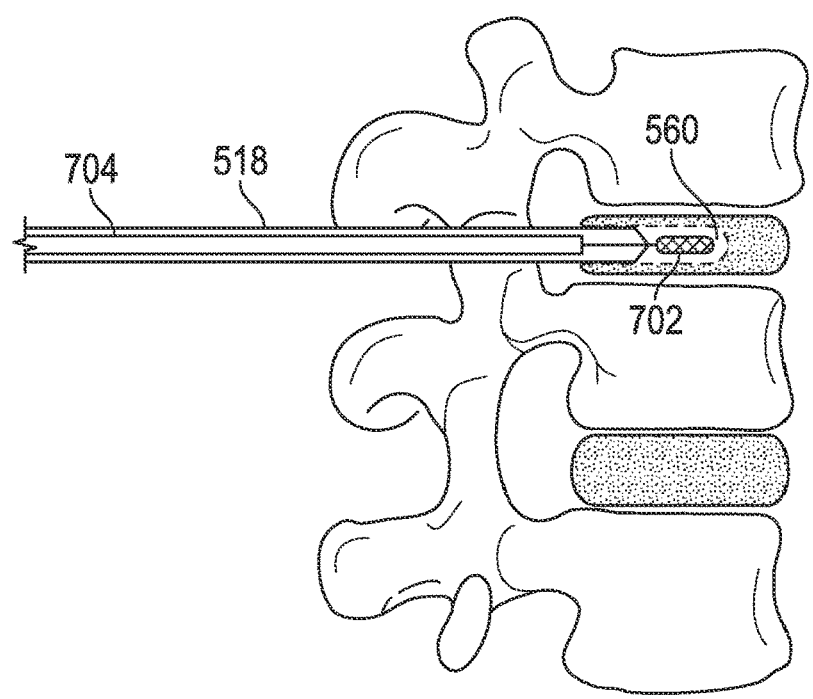
Figure 7C:
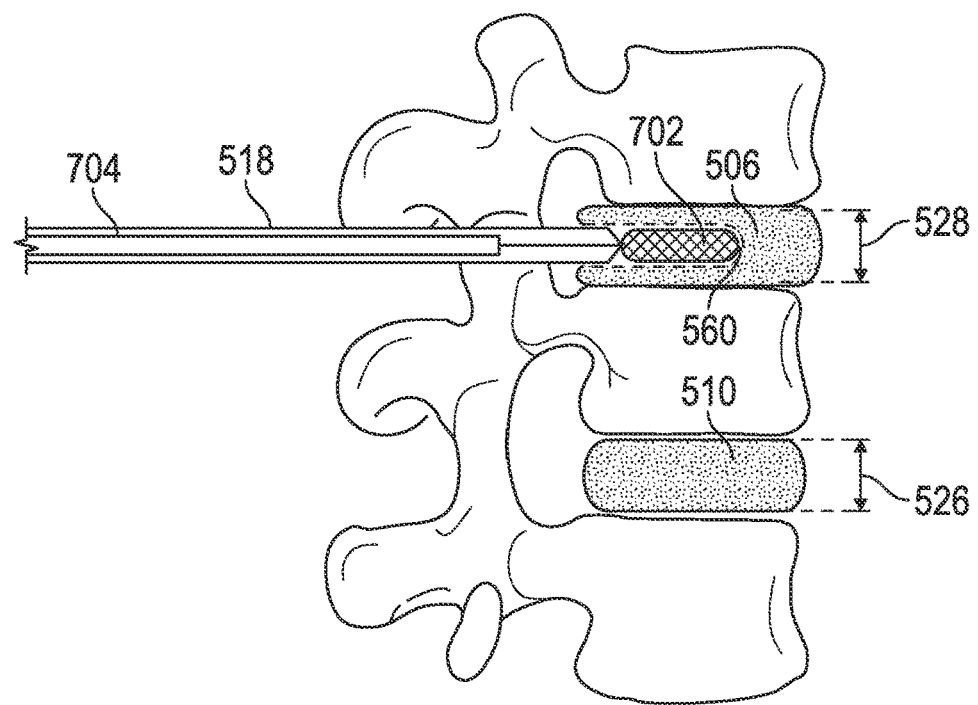
Figure 7D:
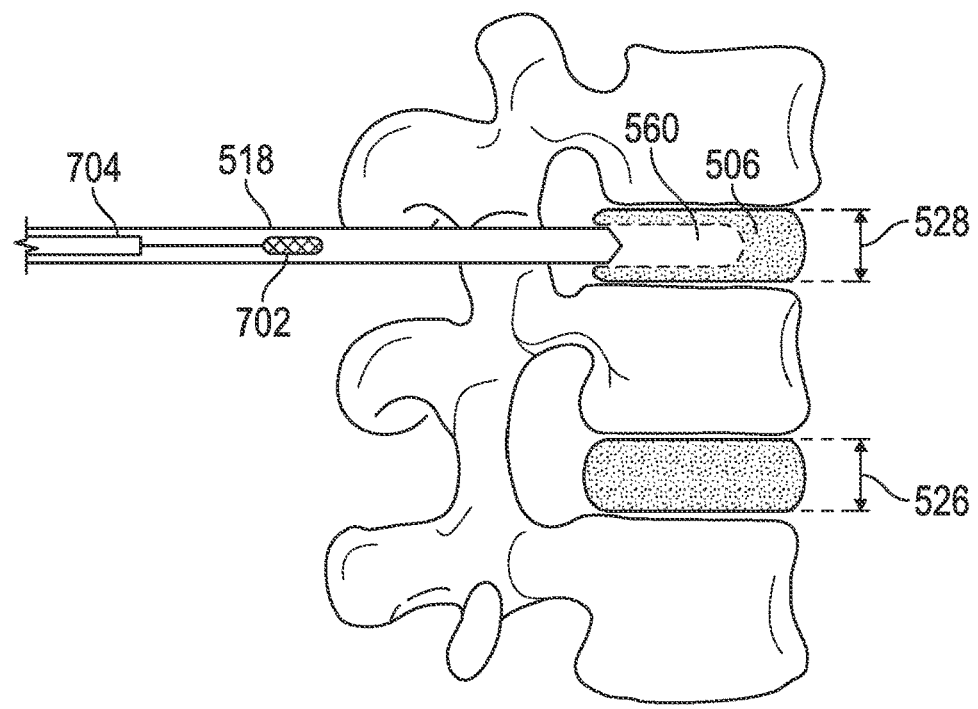
Figure 7E:
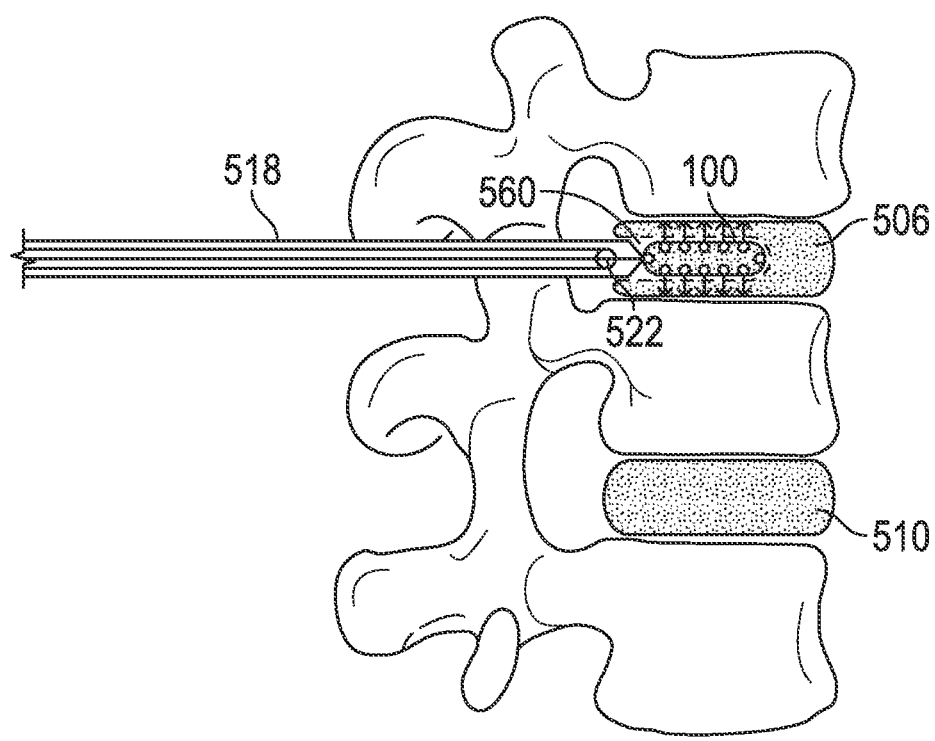

As shown in FIGS. 7A-E, in another method for deploying the intervertebral disc implant 100 into the nucleus space 560, the height 528 of the intervertebral disc space 516 may be expanded prior to deployment of the intervertebral disc implant 100 using a suitable orthopaedic balloon system 702/704. For example, the orthopaedic balloon system 702/704 may be the same as or similar to that used in balloon kyphoplasty procedures for repairing vertebral compression fractures, such as a Kyphon® Balloon (Medtronic Spinal and Biologics, Sunnyvale, Calif.). Generally, a deflated orthopaedic balloon 702 may be guided through the trocar-cannula 518 into the intervertebral space 516 (FIGS. 7A and 7B). The orthopaedic balloon 702 may then be at least partially inflated with air or an appropriate liquid, such as a sterile saline solution, to increase the intervertebral disc space height 528 (FIG. 7C). The orthopaedic balloon 702 may then be deflated and removed from the intervertebral space 516 and the trocar-cannula 518 (FIG. 7D). After removal of the orthopaedic balloon, the delivery cannula 524 may then be inserted into the trocar-cannula 518. After expansion of the intervertebral disc space height 528, the intervertebral disc implant 100 may be deployed into the nucleus space 560 as shown in FIG. 5 (FIG. 7E).

In some embodiments of the present technology, the fill material may be added to the intervertebral disc implant 100 post-operatively. For example, referring to FIG. 5I, the growth matrix and/or the additive may be added to the intervertebral disc implant 100 through a needle 530 inserted into the patient's skin and guided into the valve 120 and/or the self-sealing septum 135. In some embodiments, the needle 530 may be inserted into the valve 120 and/or the self-sealing septum in a fluoroscopically, x-ray, or other image-guided procedure.

Figure 5J:
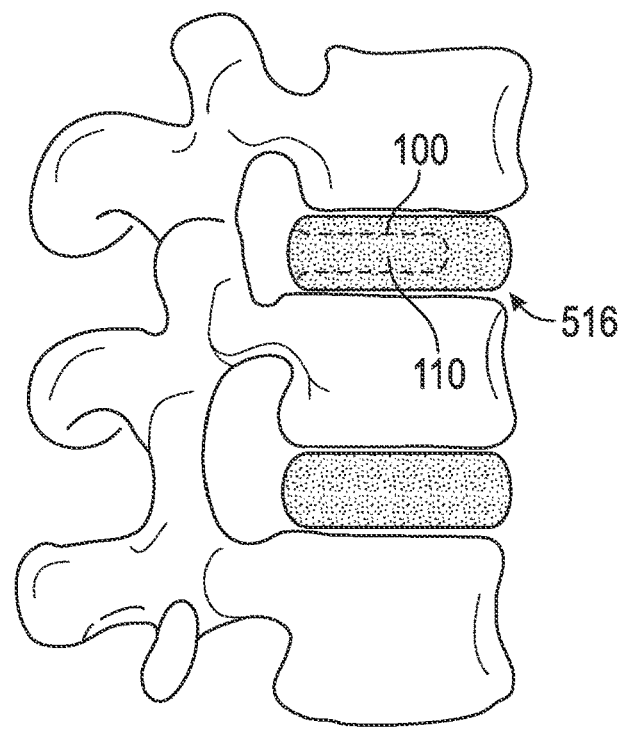

In various embodiments of the present technology, the expandable pouch 105 of the intervertebral disc implant 100 may at least partially dissolve in the intervertebral disc space 516 (FIG. 5J). As the expandable pouch 105 dissolves, the growth matrix in the lumen 110 may be exposed to the intervertebral disc space 516. As a result, the growth matrix may become more firmly attached within the natural borders of the intervertebral disc space 516.

In the foregoing description, the invention has been described with reference to specific exemplary embodiments. Various modifications and changes may be made, however, without departing from the scope of the present technology as set forth. The description and figures are to be regarded in an illustrative manner, rather than a restrictive one and all such modifications are intended to be included within the scope of the present technology. Accordingly, the scope of the invention should be determined by the generic embodiments described and their legal equivalents rather than by merely the specific examples described above. For example, the steps recited in any method or process embodiment may be executed in any appropriate order and are not limited to the explicit order presented in the specific examples. Additionally, the components and/or elements recited in any system embodiment may be combined in a variety of permutations to produce substantially the same result as the present technology and are accordingly not limited to the specific configuration recited in the specific examples.

Benefits, other advantages and solutions to problems have been described above with regard to particular embodiments. Any benefit, advantage, solution to problems or any element that may cause any particular benefit, advantage or solution to occur or to become more pronounced, however, is not to be construed as a critical, required, or essential feature or component.

The terms "comprises," "comprising," or any variation thereof, are intended to reference a non-exclusive inclusion, such that a process, method, article, composition, system, or apparatus that comprises a list of elements does not include only those elements recited, but may also include other elements not expressly listed or inherent to such process, method, article, composition, system, or apparatus. Other combinations and/or modifications of the above-described structures, arrangements, applications, proportions, elements, materials, or components used in the practice of the present technology, in addition to those not specifically recited, may be varied or otherwise particularly adapted to specific environments, manufacturing specifications, design parameters, or other operating requirements without departing from the general principles of the same.

The present technology has been described above with reference to exemplary embodiments. Changes and modifications may be made to the exemplary embodiments, however, without departing from the scope of the present technology. These and other changes or modifications are intended to be included within the scope of the present technology.

What is claimed is:

1. A system for at least partially restoring height of a compressed intervertebral disc space and healing a deranged intervertebral disc between a superior vertebra and an inferior vertebra in a spine, comprising:
   a growth matrix; and
   an intervertebral disc implant configured to at least one of repair and replace the deranged intervertebral disc to facilitate movement and flexibility within the spine, the intervertebral disc implant, comprising:
      an expandable pouch comprising:
         a pouch wall at least partially permeable to the growth matrix that defines a lumen, wherein:
            a first portion of the pouch wall is permeable to the growth matrix across at least one of a superior surface and an inferior surface of the expandable pouch, wherein the first portion of the pouch wall comprises a plurality of pores permeable to the growth matrix, wherein the distribution of pores across the expandable pouch directs permeation of the growth matrix into the intervertebral disc space toward at least one of the superior vertebra and the inferior vertebra;
            a second portion of the pouch wall is less permeable to the growth matrix across a lateral surface of the expandable pouch than the at least one of the superior surface and the inferior surface; and
            the first portion and the second portion of the pouch wall are both made of the same material which dissolves in the intervertebral disc space; and
   wherein the intervertebral disc implant provides movement and flexibility to the spine where the intervertebral disc implant is placed between the superior vertebra and the inferior vertebra and after the intervertebral disc implant is filled with the growth matrix.

2. The system of claim 1, wherein the second portion of the pouch wall is substantially impermeable to the growth matrix.

3. The system of claim 1, wherein the expandable pouch further comprises a fill port disposed through a posterior surface of the expandable pouch, wherein the fill port provides access to the lumen of the expandable pouch for filing with the growth matrix.

4. The system of claim 3, wherein the fill port is configured to provide postoperative access to the lumen of the expandable pouch for refilling with the growth matrix.

5. The system of claim 1, wherein the expandable pouch is deflatable to fit inside a surgical trocar-cannula having an inner diameter of less than approximately 20 millimeters.

6. The system of claim 1, wherein the expandable pouch is at least one of partially inflated and over-distended upon filling with the growth matrix.

7. The system of claim 1, wherein the expandable pouch comprises an at least partially self-assembling modular material configured to self-assemble into a spiral-form upon delivery into the intervertebral disc space.

8. The system of claim 7, wherein the at least partially modular self-assembling material comprises interconnected chambers.

9. The system of claim 1, wherein the expandable pouch further comprises a radiopaque material for imaging.

10. The system of claim 1, further comprising:
    a delivery device for surgically implanting the intervertebral disc implant into the intervertebral disc space, wherein the delivery device is configured to:
       couple to the intervertebral disc implant,
       insert the intervertebral disc implant into the intervertebral disc space from a percutaneous position, and
       release the intervertebral disc implant into the intervertebral disc space.

11. The system of claim 10, wherein the delivery device is further configured to travel through a trocar-cannula to reach the intervertebral disc space.

12. The system of claim 1, wherein the inflated intervertebral disc implant approximates the size of a nucleus propulsus of the intervertebral disc.

13. The system of claim 12, wherein the inflated intervertebral disc implant is at least approximately 1 inch long, at least approximately 0.5 inches wide, and at least approximately 0.25 inches in height.

14. The system of claim 1, wherein the first portion allows the growth matrix to at least one of diffuse and grow from the lumen of the expandable pouch, out through the pores, and into the intervertebral disc space.

15. The system of claim 14, wherein the permeability of the first portion is effected by at least one of a diameter of a plurality of pores and a chemical structure of the pores.

16. The system of claim 15, wherein the pores have a diameter of approximately 10 μm.

17. The system of claim 1, further comprising a nutrient capsule disposed within the lumen of the expandable pouch.

18. The system of claim 1, wherein distribution of the pores is arranged in a gradient with the highest concentration of pores located on the superior surface and the inferior surface and the concentration of pores decreasing according to the gradient toward the lateral surface of the expandable pouch resulting in less permeability across the lateral surface as compared to at least one of the superior surface and the inferior surface.

19. A system for surgically repairing an intervertebral disc derangement in an intervertebral disc space between a superior vertebra and an inferior vertebra in a spine, comprising:
    a growth matrix;

an intervertebral disc implant configured to at least one of repair and replace the deranged intervertebral disc to facilitate movement and flexibility within the spine, wherein the intervertebral disc implant forms an expandable pouch that dissolves in the intervertebral disc space, the intervertebral disc implant comprising:
  a lumen configured to be filled with the growth matrix; and
  a plurality of pores that are permeable to the growth matrix, wherein:
    the pores are distributed across at least one of a superior surface and an inferior surface of the expandable pouch to provide directional permeability of the growth matrix out of the expandable pouch into the intervertebral disc space, and
    the distribution of the pores is arranged in a gradient with the highest concentration of pores located on the superior surface and the inferior surface and the concentration of pores decreases according to the gradient toward a lateral surface of the expandable pouch resulting in provide less permeability across the lateral surfaces as compared to at least one of the superior surface and the inferior surface;
  wherein the lateral surface, the superior surface, and the inferior surface are the same dissolvable material; and
  wherein the intervertebral disc implant provides flexibility to the spine where the intervertebral disc implant is placed between the superior vertebra and the inferior vertebra and after the intervertebral disc implant is filled with the growth matrix.

20. The system of claim 19, wherein the expandable pouch further comprises a fill port disposed through a posterior surface of the expandable pouch, wherein the fill port provides postoperative access to the lumen of the expandable pouch for refilling with the growth matrix.

21. The system of claim 19, wherein the expandable pouch is deflatable to fit inside a surgical trocar-cannula having an inner diameter of less than approximately 20 millimeters.

22. The system of claim 21, wherein the expandable pouch is at least one of partially inflated and over-distended upon filling with the growth matrix.

23. The system of claim 19, further comprising:
  a delivery device for surgically implanting the intervertebral disc implant into the intervertebral disc space, wherein the delivery device is configured to:
    couple to the intervertebral disc implant,
    insert the intervertebral disc implant into the intervertebral disc space from a percutaneous position, and
    release the intervertebral disc implant into the intervertebral disc space.

24. The system of claim 19, wherein the pores allow the growth matrix to at least one of diffuse and grow from the lumen of the expandable pouch, out through the pores, and into the intervertebral disc space.

25. The system of claim 24, wherein the permeability of the pores is effected by at least one of a diameter of a plurality of pores and a chemical structure of the pores.

26. A method for surgically repairing an intervertebral disc derangement in a compressed intervertebral disc space between a superior vertebra and an inferior vertebra with a growth matrix, comprising:
  accessing the compressed intervertebral disc space percutaneously;
  removing at least a portion of the deranged intervertebral disc leaving an at least partially evacuated intervertebral disc space;
  implanting an intervertebral disc implant comprising an expandable pouch into the at least partially evacuated intervertebral disc space, wherein the expandable pouch comprises:
    a lumen configured to be filled with the growth matrix; and
    a plurality of pores that are permeable to the growth matrix, wherein:
      the distribution of the pores provide permeability across at least one of the superior surface and the inferior surface of the expandable pouch, and
      the distribution of the pores provide less permeability across the lateral surfaces of the expandable pouch as compared to at least one of the superior surface and the inferior surface; and
  filling the expandable pouch with the growth matrix,
  wherein the intervertebral disc implant provides movement and flexibility to the spine where the intervertebral disc implant is placed between the superior vertebra and the inferior vertebra and after the intervertebral disc implant is filled with the growth matrix.

27. The method of claim 26, wherein the removed portion of the deranged intervertebral disc comprises at least part of the nucleus pulposus.

28. The method of claim 26, further comprising expanding the compressed intervertebral disc space prior to deployment of the intervertebral disc implant into the at least partially evacuated intervertebral disc space.

* * * * *